US010987047B2

(12) United States Patent
Principe et al.

(10) Patent No.: US 10,987,047 B2
(45) Date of Patent: *Apr. 27, 2021

(54) SYSTEM AND METHOD FOR ANALYZING PROGRESS OF LABOR AND PRETERM LABOR

(71) Applicants: Convergent Engineering, Inc., Gainesville, FL (US); University of Florida Research Foundation, Inc., Gainesville, FL (US)

(72) Inventors: Jose C. Principe, Gainesville, FL (US); Dorothee Maroserro, Paris (FR); Tammy Y. Euliano, Gainesville, FL (US); Neil Russell Euliano, II, Gainesville, FL (US)

(73) Assignees: Convergent Engineering, Inc., Gainesville, FL (US); University of Florida Research Foundation, Inc., Gainesville, FL (US)

(*) Notice: Subject to any disclaimer, the term of this patent is extended or adjusted under 35 U.S.C. 154(b) by 264 days.

This patent is subject to a terminal disclaimer.

(21) Appl. No.: 15/967,296

(22) Filed: Apr. 30, 2018

(65) Prior Publication Data
US 2019/0125246 A1 May 2, 2019

Related U.S. Application Data

(63) Continuation of application No. 13/443,161, filed on Apr. 10, 2012, now Pat. No. 9,974,474, which is a (Continued)

(51) Int. Cl.
A61B 5/00 (2006.01)
A61B 5/0488 (2006.01)
(Continued)

(52) U.S. Cl.
CPC ........ A61B 5/4356 (2013.01); A61B 5/04882 (2013.01); A61B 5/1107 (2013.01);
(Continued)

(58) Field of Classification Search
CPC . A61B 5/04882; A61B 5/0444; A61B 5/4356; A61B 5/7203; A61B 5/04085;
(Continued)

(56) References Cited

U.S. PATENT DOCUMENTS 3,010,233 A 11/1961 Wells et al.
3,703,168 A 11/1972 Frink
(Continued)

FOREIGN PATENT DOCUMENTS

WO WO-2006056221 A1 * 6/2006 ......... G01S 15/8979

OTHER PUBLICATIONS

Acog Practice Bulletin No. 49, Dec. 2003: Dystocia and Augmentation of Labor. Obstetrics & Gynecology 2003; vol. 102, No. 6; 1445-1454.
(Continued)

Primary Examiner — Patrick Fernandes

(57) ABSTRACT

Systems and methods for monitoring uterus contraction activity and progress of labor. The system of the subject invention can comprises (1) a plurality of sensors; (2) an amplifying/filtering means; (3) a computing means; and (4) a graphical user interface. Accurate clinical data, which can be extracted and provided to the user in real-time using the system of the invention, include without limitation, progress of labor, prediction and monitoring of preterm labor, and intrauterine pressure prediction. In a preferred embodiment, the system of the invention includes an intelligence means, such as a neural network system, to analyze and interpret clinical data for use in clinical diagnosis as well as delivery strategy.

20 Claims, 22 Drawing Sheets

Related U.S. Application Data continuation of application No. 12/475,911, filed on Jun. 1, 2009, now Pat. No. 8,160,692, which is a continuation-in-part of application No. PCT/US2007/025495, filed on Dec. 11, 2007.

(60) Provisional application No. 60/874,153, filed on Dec. 11, 2006.

(51) Int. Cl.
    *A61B 5/11* (2006.01)
    *G16Z 99/00* (2019.01)
    *G06F 19/00* (2018.01)

(52) U.S. Cl.
    CPC .............. *G06F 19/00* (2013.01); *G16Z 99/00* (2019.02); *A61B 5/7264* (2013.01); *A61B 2503/02* (2013.01); *A61B 2562/046* (2013.01)

(58) Field of Classification Search
    CPC . A61B 5/1107; A61B 5/7264; A61B 2503/02; A61B 2562/046; G16Z 99/00; G06F 19/00
    See application file for complete search history.

(56) References Cited

U.S. PATENT DOCUMENTS

| | | | |
|---|---|---|---|
| 4,256,118 A | | 3/1981 | Nagel |
| 4,967,761 A | | 11/1990 | Nathanielsz |
| 5,301,680 A | * | 4/1994 | Rosenberg ......... A61B 5/04882 128/903 |
| 5,397,344 A | | 3/1995 | Garfield et al. |
| 5,483,970 A | | 1/1996 | Rosenberg |
| 5,546,953 A | | 8/1996 | Garfield |
| 5,623,939 A | | 4/1997 | Garfield |
| 5,785,664 A | | 7/1998 | Rosenberg |
| 2002/0193670 A1 | * | 12/2002 | Garfield ............. A61B 5/04882 600/304 |
| 2003/0199749 A1 | | 10/2003 | Lowery, Jr. et al. |
| 2005/0267376 A1 | * | 12/2005 | Marossero ........... A61B 5/0444 600/511 |
| 2005/0267377 A1 | * | 12/2005 | Marossero ......... A61B 5/02411 600/511 |
| 2009/0012432 A1 | | 1/2009 | Sharf |

OTHER PUBLICATIONS

Agarwal, N., et al., "Role of Uterine Artery Velocimetry Using Color-Flow Doppler and Electromyography of Uterus in Prediction of Preterm Labor," J. Obstet. Gynaecol. Res., 2004, pp. 402-408, vol. 30.
Albers, L.L., et al., "The Length of Active Labor in Normal Pregnancies,"Obstetrics and Gynecology, 1996, pp. 355-359, vol. 87.
Allman, A,C., etal., "Head-to-Cervix Force: An Important Physiological Variable in Labour. 2 Peak Active Force, Peak Active Pressure and Mode of Delivery," BJOG, 1996, pp. 769-775, vol. 103.
Althaus, J.E., et al.. "Cephalopelvic Disproportion is Associated with an Altered Uterine Contraction Shape in the Active Phase of Labor," Am, J. Obstet. Gynecol, 2006, pp. 739-742, vol. 195.
Buhimschi, C. et al., "Electrical Activity of the Human Uterus During Pregnancy as Recorded from the Abdominal Surface," Obstet, Gynocol., 1997, pp. 102-111, vol. 90.
Caldeyro, R., et al., "A Better Understanding of Uterine Contractility Through Simultaneous Recording with an Internal and a Seven Channel External Method," Surger Gynecology & Obstetrics, 1950, pp. 641-650, vol. 91.
Crane, J.M., "Factors Predicting Labor Induction Success: A Critical Analysis," C/in. Obstet. Gynecol., 2006, pp. 573-584, vol. 49.
Devedeux, D., et al., "Uterine Electromyography: A Critical Review," Am. J. Gynecol., 1993, vol. 169, pp. 1636-1653.
Dujardin B. et al., "Value of the Alert and Action Lines OH the Partogram"; Lancet 1992; 339: 1336-8.
Eswaran, H., et al., "First Magnetomyographic Recording of Uterine Activity with Spatial-Temporal Information with a 151-Channel Sensor Array," Am. J. Obstet. Gynecol, 2002; vol. 187; pp. 145-151.
Euliano, T., et al., "Prediction of Intrauterine Pressure Waveform from Transabdominal Electrohysterography," Journal of Maternal-Fetal & Neonatal Medicine, 2006, vol. 19, No. 12, pp. 803-808.
Farine, D., et al., "The Need for a New Outlook on Labor Monitoring," Journal of Maternal-Fetal & Neonatal Medicine, 2006, vol. 19, pp. 161-164.
Feinstein, U., et al., "Risk Factors for Arrest of Descent During the Second Stage of Labor," International Journal of Gynecology & Obstetrics, 2002, vol. 77, pp. 7-14.
Friedman E.; "Cervimetry—An Objective Method for the Study of Cervical Dilatation in Labor"; American Journal of Obstetrics and Gynecology 1956; 71: 1189-1193.
Garfield, R,E., et al., "Comparing Uterine Electromyography Activity of Antepartum Patients Versus Term Labor Patients," Am. J. Obstet. Gynecol., 2005, vol. 193, pp. 23-29.
Guyer B. et al.; "Annual Summary of Vital Statistics 1996", Pediatrics 1997, 100(6):905-918.
Hamilton, B.E. et al.; "Preliminary births for 2004: Infant and maternal health"; Health B-stats; National Center for Health Statistics 54(2). Sep. 8, 2005.
Hasegawa, I., et al., "Transvaginal Ultrasonographic Cervical Assessment for the Prediction of Preterm Delivery," J. Maternal-Fetal Medicine, 1996, pp. 305-309, vol. 5. Abstract Only.
Healthy People 2010; Maternal, Infant, and Child Health [online] [retrieved Sep. 22, 2017]. Retrieved from the Internet:<URL:https://web.archive.org/web/20060925231111/https://www.healthypeople.gov/document/html/volume2/16mich.htm>. 52 pages.
Hellman, L.M., et al., "Characteristics of the Gradients of Uterine Contractility During the 1 Stage of True Labor," Bull Johns Hopkins Hosp., 1951, pp. 13-15, vol. 6, No. 1.
Hin, L.Y., etal., "Anteparturn and Intrapartum Prediction of Cesarean Need: Risk Scoring in Singleton Pregnancies," Obstetrics and Gynecology, 1997, pp. 183-186, vol. 90.
Iams, J.D., et al., "Cervical Competence as a Continuum: A Study of Ultrasonographic Cervical Length and Obstetrical Performance," American Journal of Obstetrics and Gynecology, 1995, pp. 1097-1106, vol. 172.
International Search Report and Written Opinion from International Patent Application No. PCT/US2007/025495, dated Apr. 30, 2008, 6 pages.
Jezewski, J., et al., "Quantitative Analysis of Contraction Patterns in Electrical Activity Signal of Pregnant Uterus as an Alternative to Mechanical Approach," Physiol Meas., 2005, pp. 753-767, vol. 26.
Kwast Be et al.; "World-Health-Organization Partograph in Management of Labor"; Lancet 1994; 343: 1399-1404.
Landon, MB., et al., "Maternal and Perinatal Outcomes Associated with a Trial of Labor After Prior Cesarean Delivery," N. Engl. J. Med., 2004, pp. 2581-2589, vol. 351.
Maner, W.L., et al., "Predicting Term and Preterm Delivery with Transabdominal Uterine Electromyography," Obstet. Gynecol., 2003, pp. 1254-1260, vol. ioi.
Mansour, S., et al, "Uterine EMG Spectral Analysis and Relationship to Mechanical Activity in Pregnant Monkeys," Med. Blot Eng., 1996, pp. 115-121, vol. 34. Abstract Only.
Margono, F. et al., "Intrauterine Pressure Wave Charateteristics of the Upper and Lower Uterine Segments in Parturients with Active-Phase Arrest," Obstetrics and Gynecology, 1993, pp. 481-485, vol. 81.
Marque et al., "Uterine EHG Processing for Obstetrical Monitoring" IEEE Transaction on Biomedical Engineering, Dec. 1986, vol. BME-33, No. 12, pp. 1182-1187.
Martin J.A. et al.; "Births: Final data for 2003"; National vital statistics reports; vol. 54, No. 2; Sep. 8, 2005; pp. 1-116.
Maul, H., etal., "Non-Invasive Transabdominal Uterine Electromyography Correlates with the Strength of Intrauterine

(56) References Cited

OTHER PUBLICATIONS

Pressure and is Predictive of Labor and Delivery," J. Matern. Fetal Neonatal Med., 2004, pp. 297-301, vol. 15.

Murakawa, H., etal., "Evaluation of Threatened Preterm Delivery by Transvaginal Ultrasonographic Measurement of Cervical Length," Obstetrics and Gynecology, 1993, pp. 829-832, vol. 82.

Peregrine, E., et al.; "Clinical and Ultrasound Parameters to Predict the Risk of Cesarean Delivery After Induction of Labor," Obstet GynecoL, 2006, pp. 227-233, vol. 107.

Phelps, J.Y., et al.; "Accuracy and Intraobserver Variability of Simulated Cervical Dilation Measurements"; American Journal of Obstetrics and Gynecology, 1995, pp. 942-945, vol. 173.

Rouse DJ et al.; "Active-phase labor arrest: oxytocin augmentation for at least 4 hours"; Obstetrics & Gynecology 1999; 93: 323-8.

Rouse, D.J., et al.; "Active Phase Labor Arrest: Revisiting the 2-Hour Minimum"; Obstetrics & Gynecology, 2001, pp. 550-554, vol. 98.

Sachs B.P. et al.; "The Risks of Lowering the Cesarean-Delivery Rate"; The New England Journal of Medicine 1999; 340: 53-61.

Seitchik, J., et al.; "Intrauterine Pressure Wave Form Characteristics of Successful and Failed 1st Stage Labor"; Gynecologic Investigation, 1977, pp. 246-253, vol. 8.

Sharf, Y., et al.; "Continuous Monitoring of Cervical Dilation and Fetal Head Station During Labor"; Medical Engineering & Physics, 2007, pp. 61-71, vol. 29.

Sheiner, E., et al.; "Obstetric Risk Factors and Outcome of Pregnancies Complicated with Early Postpartum Hemorrhage: A Population-Based Study"; J. Matern-Fetal Neonatal Med., 2005, pp. 149-154, vol. 18.

Sheiner, E., et al.; "Risk Factors and Outcome of Failure to Progress During the First Stage of Labor: A Population Based Study"; Acta Obstetricia at Gynecologic Scandinavica, 2002, pp. 222-226, vol. 81.

Skowronski, M.D., et al.; "Prediction of Intrauterine Pressure from Electrohysterography Using Optimal Linear Filtering"; IEEE-TBME, 2006, pp. 1983-1989, vol. 53.

Spatling, L., et al.; "External 4-Channel Tocography During Delivery"; International Journal of Gynecology & Obstetrics, 1994, pp. 291-295, vol. 46.

Steer, C.M., et al.; "Electrical Activity of the Human Uterus in Labor; The Electrohysterograph," Am1. J. Obstet. Gynecol., 1950, pp. 25-40, vol. 59.

Steer, C.M; "The Electrical Activity of the Human Uterus in Normal and Abnormal Labor," Am. J. Obstet. Gynecol., 1954, pp. 867-590, vol. 68.

Turcot, L., et al.; "Multivariate Analysis of Risk Factors for Operative Delivery in Nulliparous Women"; American Journal of Obstetrics and Gynecology, 1997, pp. 395-402, vol. 176.

Verdenik, I., et al.; "Uterine Electrical Activity as Predictor of Preterm Birth in Women with Preterm Contractions"; Eur. J. Obstet. Gynecol. Reprod. Blot., 2001, pp. 149-153, vol. 95.

Wikland, M., et al.; "Relationship Between Electrical and Mechanical Activity of the Isolated Term-Pregnant Human Myometrium"; Eur. J. Gynecol. Reprod. Biol., 1985, pp. 337-346, vol. 20.

Wilkes, P.T., et al.; "Risk Factors for Cesarean Delivery at Presentation of Nulliparous Patients in Labor"; Obstetrics and Gynecology, 2003, pp. 1352-1357, vol. 102.

Wolfs, G., et al.; "An Electromyographic Study of the Human Uterus During Labor"; Obstet. Gynecol., 1971; pp. 241-246, vol. 37.

Zhang, J. et al.; "Reassessing the Labor Curve in Nulliparous Women"; American Journal of Obstetrics and Gynecology, 2002, pp. 824-828, vol. 187.

\* cited by examiner

| Patient Variable | Delivery | | |
|---|---|---|---|
| | Cesarean N=12 | Vaginal N=24 | P value |
| Gestational Age (weeks) | 39.0 ± 1.7 | 38.5 ± 1.1 | 0.43 |
| Body Mass Index | 34.2 ± 6.3 | 30.4 ± 4.9 | 0.12 |
| Dilation at Monitoring (cm) | 7.0 ± 1.7 | 7.4 ± 1.2 | 0.51 |
| Newborn Weight (g) | 3479 ± 512 | 3131 ± 372 | 0.07 |
| Maternal Age (years) | 24.1 ± 4.8 | 23.4 ± 5.2 | 0.73 |
| Duration of arrest (hours) | 6.1 ± 3.1 | | |
| Montevideo Unit Maximum (mmHg) | 255 ± 70 | | |
| Oxytocin Augmentation | 100% | 71% | |
| Epidural Use | 100% | 96% | |

FIG. 15

SYSTEM AND METHOD FOR ANALYZING PROGRESS OF LABOR AND PRETERM LABOR

CROSS-REFERENCE TO RELATED APPLICATIONS

This application is a continuation of U.S. application Ser. No. 13/443,161, filed Apr. 10, 2012, which is a continuation of U.S. application Ser. No. 12/475,911, filed Jun. 1, 2009, now U.S. Pat. No. 8,160,692; which is a continuation-in-part application of International Application No. PCT/US2007/025495, filed Dec. 11, 2007; which claims the benefit of U.S. Provisional Application Ser. No. 60/874,153, filed on Dec. 11, 2006, all of which are incorporated herein by reference in their entirety.

GOVERNMENT SUPPORT

This invention was made with government support under a grant awarded from the National Science Foundation under grant number 0239060. The government has certain rights in the invention.

BACKGROUND OF INVENTION

The definition of labor is 'the presence of uterine contractions of sufficient intensity, frequency, and duration to bring about demonstrable effacement and dilation of the cervix.' See ACOG Practice Bulletin Number 49, December 2003: Dystocia and Augmentation of Labor. Obstetrics & Gynecology 2003; 102: 1445-54. From a clinical perspective, the characteristics of an efficient contraction are: (1) Pressure above 25 mm and regularity in intensity; (2) Frequency greater than 2 per 10 minutes and regularity in frequency; (3) Fundal dominance (contraction over the fundus and no appreciable contraction over the cervix); (4) Synchronization and fast propagation over the uterus. Currently progress of labor is determined by serial cervical exam to assess dilation, effacement and station.

In 2004 the cesarean delivery rate was 29.1% of all births, a new high for the U.S. (Martin J A et al. Preliminary births for 2004: Infant and maternal health. Health E-stats. National Center for Health Statistics. 11-15-0005) and well above the government's Healthy People 2000 goal of 15%. Unfortunately, the cesarean delivery rate continues to rise (6% in 2003-4), due both to an increase in the primary cesarean rate and a decrease in the rate of vaginal birth after cesarean (VBAC).

Labor Dystocia

The indications for cesarean delivery are varied, but dystocia (lack of progress in labor) leads the list. Dystocia is a labor abnormality resulting in abnormal progression and may be due to problems with power (uterine contractions and/or maternal expulsive effort), passenger (position or size of the fetus), or passage (shape or size of the birth canal). Early diagnosis and management of power problems are one of the concerns of this invention. If there are no contraindications (e.g., previa), protracted or arrested labors are often augmented with oxytocin. The goal of augmentation is to achieve minimally effective uterine activity; however, this is poorly defined and certainly inconsistent among parturients. Several groups have attempted to predict either antepartum, or early intrapartum, which patients are destined to have a labor dystocia. Unfortunately these efforts have met with little success. See Sheiner E et al. Risk factors and outcome of failure to progress during the first stage of labor: a population-based study. Acta Obstetricia et Gynecologica Scandinavica 2002; 81: 222-6; Feinstein U et al., Risk factors for arrest of descent during the second stage of labor. International Journal of Gynecology & Obstetrics 2002; 77: 7-14; Wilkes P T et al., Risk factors for cesarean delivery at presentation of nulliparous patients in Labor. Obstetrics and Gynecology 2003; 102: 1352-7; Turcot L et al., Multivariate analysis of risk factors for operative delivery in nulliparous women. American Journal of Obstetrics and Gynecology 1997; 176: 395-402; and Hin L Y et al., Antepartum and intrapartum prediction of cesarean need: Risk scoring in singleton pregnancies. Obstetrics and Gynecology 1997; 90: 183-6.

While most believe the cesarean delivery rate excessive, there is concern over efforts to reduce it. A litany of editorials followed an article in the *New England Journal of Medicine* arguing against aggressive reduction of cesareans (Sachs B P et al., The Risks of Lowering the Cesarean-Delivery Rate. The New England Journal of Medicine 1999; 340: 54-7). The subsequent Healthy People 2010 goals limit their focus on reducing the cesarean rate among only low risk patients (CDC and HRSA. Healthy People 2010: Maternal, Infant, and Child Health. http://www.healthypeople.gov/document/html/volume2/16mich.htm#_Toc494699664 (2006) 9-13-0006). The VBAC target is separately listed as 63%, quite distant from the rate of 10.6% reported in 2003 (Martin J A et al., Births: Final data for 2003. National vital statistics reports. National Center for Health Statistics 54(2). Sep. 8, 2005. Hyattsville, Md. Sep. 13, 2006). In fact the VBAC rate has actually fallen by nearly two-thirds since 1996, in large part due to safety concerns (Landon M B et al., the National Institute of Child Health and Human Development Maternal-Fetal Medicine Units Network: Maternal and Perinatal Outcomes Associated with a Trial of Labor after Prior Cesarean Delivery. The New England Journal of Medicine 2004; 351: 2581-9). Women who labor and then fail to deliver vaginally have more complications (primarily infection and hemorrhage), incur more expense, and consume more resources (labor suite, nurse, etc.) than women who have an elective abdominal delivery. For VBAC patients, who are at increased risk for labor dystocia, the risk of uterine rupture increases the potential for a catastrophic outcome, and elective repeat cesareans are becoming the standard.

With declining numbers of patients attempting a subsequent vaginal birth after cesarean (VBAC), 60% of cesareans may relate directly or indirectly to the diagnosis of dystocia. The diagnosis of dystocia, however, is a matter of debate since, if given enough time, many very slow and even arrested labors will eventually proceed to vaginal delivery.

Preterm Labor

Preterm delivery is the most common cause of perinatal morbidity and mortality in infants without congenital anomalies. Over 11% of all births are preterm, and the complications of prematurity cause more than 70% of the deaths of nonanomalous fetuses and neonates (Gruyer B. et al. Annual Summary of Vital Statistics—1996. *Pediatrics* 1997, 100(6):905-918).

Many studies have shown an association between having a short cervix on ultrasound and an increased risk of preterm delivery (Hasegawa I et al. Transvaginal ultrasonographic cervical assessment for the prediction of preterm delivery. *Journal of Maternal and Fetal Medicine* 1996, 5: 305-309; Murakawa H et al., Evaluation of threatened preterm delivery by transvaginal ultrasonographic measurement of cervical length. *Obstetrics and Gynecology* 1993, 82: 829-832; and Iams J D et al., Cervical competence as a continuum: a study of ultrasonographic cervical length and obstetrical performance *American Journal of Obstetrics and Gynecology*, 1995, 172: 1097-1106). However neither this, nor any other test has proven sufficiently reliable for prediction.

Uterine Monitoring

The uterus is different from other visceral smooth muscles because it has no nerve plexus; it has no peristaltic waves, yet it displays tonus (contraction without shortening). Throughout most of pregnancy, the uterine contractions are minor and intensely localized. Only in the second half of gestation does the tendency for major contractions develop. These non-painful 'Braxton Hicks' contractions involve a large part or all of the myometrium, but usually lack the high degree of coordination that one finds during labor.

It is important to understand the impact of contractions on intrauterine pressure. Even when the uterus is relaxed its contents are under minimal pressure: the 'diastolic uterine pressure.' During contractions the intrauterine pressure increase depends on the elastic properties of the tissue and the active force exerted by the contractions of the myometrium. If the activity of the uterine musculature is coordinated and strong, the increase in pressure can be substantial ('systolic uterine pressure'). However, if the coordination is weak, the same contraction strength gives rise to an overall increase of tonus reflected in an increase of systolic pressure. Intrauterine pressure, however, does not represent the direction or orientation of the forces acting on the fetus. It is known, for instance, that forces pushing down on the fetus (fundal uterine dominance) are more important to produce cervical dilation.

Cervical dilatation is the most important indicator of labor progress. The partogram—a graph of cervical dilation versus time—has been promoted by the World Health Organization for management of labor and recognition of abnormal progress (Rouse D J et al., Active-phase labor arrest: oxytocin augmentation for at least 4 hours. Obstetrics & Gynecology 1999; 93: 323-8). This graph has an 'alert line' at an active phase dilation rate of 1 cm/hour, used to guide transfer to a larger hospital and/or augmentation. More widely employed elsewhere in the world, use of the partogram may improve outcomes for both mother and fetus (Kwast B E et al., World-Health-Organization Partograph in Management of Labor. Lancet 1994; 343: 1399-404). The traditionally quoted $5^{th}$ percentile of normal progress in spontaneous term labor is 1.2 cm/h for nulliparas and 1.5 cm/h for multiparas (Dujardin B et al., Value of the Alert and Action Lines on the Partogram. Lancet 1992; 339: 1336-8). However, these numbers have been challenged recently, with the $5^{th}$ percentile for nulliparas recorded at <1 cm/hr, and periods of arrested dilation before 7 cm commonly seen (Friedman E A: Cervimetry—An Objective Method for the Study of Cervical Dilatation in Labor. American Journal of Obstetrics and Gynecology 1956; 71: 1189-93). Unfortunately, the inaccuracy of cervical dilation assessment severely limits the ability to detect a real change of one, or even two centimeters (Zhang J et al., Reassessing the labor curve in nulliparous women. American Journal of Obstetrics and Gynecology 2002; 187: 824-8). This may lead to incorrect conclusions regarding progress of labor in up to 33% of those progressing at 1 cm/hr, if checked at 2 hour intervals (Phelps J Y et al., Accuracy and intraobserver variability of simulated cervical dilatation measurements. American Journal of Obstetrics and Gynecology 1995; 173: 942-5).

Intrauterine pressure catheters (IUPCs) are currently used to measure the intra uterine pressure during rest (diastole) and during contraction (systole). However, it is impossible with an intra ovular method to distinguish different patterns of coordination over the uterus and also spatial characteristics of the contraction such as fundal dominance.

There are however, external methods to measure the local activity of the myometrium. Tocodynamometers can be applied externally over the mother's abdominal region and provide a local estimate of the changes in pressure, but not the internal pressure nor tonus. This is the most commonly employed uterine activity monitor.

Electrohysterography

It is well-established that uterine contractions are the result of uterine electrical activity (Wolfs G et al., An electromyographic study of the human uterus during labor. Obstet. Gynecol. 1971; 37: 241-6; and Wikland M, Lindblom B: Relationship between electrical and mechanical activity of the isolated term-pregnant human myometrium. Eur. J. Obstet. Gynecol. Reprod. Biol. 1985; 20: 337-46). This electrical activity can be observed non-invasively from the surface of the maternal abdomen and has been described in some detail (Buhimschi C et al., Electrical activity of the human uterus during pregnancy as recorded from the abdominal surface. Obstet. Gynecol. 1997; 90: 102-11; Jezewski J et al., Quantitative analysis of contraction patterns in electrical activity signal of pregnant uterus as an alternative to mechanical approach. Physiol Meas. 2005; 26: 753-67; Devedeux D et al., Uterine electromyography: a critical review. Am. J. Obstet. Gynecol. 1993; 169: 1636-53; and Mansour S et al., Uterine EMG spectral analysis and relationship to mechanical activity in pregnant monkeys. Med. Biol. Eng Comput. 1996; 34: 115-21). As early as 1950, this electrohysterogram (EHG) was found to discriminate between normal labor and 'uterine inertia.' See Steer C M, Hertsch G J: Electrical activity of the human uterus in labor; the electrohysterograph. Am. J Obstet Gynecol 1950; 59: 25-40; and Steer C M: The electrical activity of the human uterus in normal and abnormal labor. Am. J Obstet Gynecol 1954; 68: 867-90. Recently there has been renewed interest in the potential of EHG.

Several studies have investigated the utility of EHG in predicting preterm delivery. Verdenik et al. (Uterine electrical activity as predictor of preterm birth in women with preterm contractions. Eur. J. Obstet. Gynecol. Reprod. Biol. 2001; 95: 149-53) studied 47 women who presented with complaint of preterm contractions who were admitted either for tocodynamometer (toco) confirmation of contractions or for closer monitoring due to additional risk factors. Using two paramedian electrodes referenced to a ground, the filtered EMG was acquired for 30 minutes. The intensity of electrical activity was calculated as the root mean square (RMS) value of the entire signal. They also determined the median frequency of the power spectra, but only the RMS value differed in those patients who would deliver preterm (n=17) and those who reached term (n=30).

Agarwal et al. (Role of uterine artery velocimetry using color-flow Doppler and electromyography of uterus in prediction of preterm labor. J. Obstet. Gynaecol. Res. 2004; 30: 402-8) studied 100 patients at 24-32 weeks gestation at high risk for preterm labor and compared ultrasound cervical length measurement, uterine artery velocimetry and EHG in the prediction of labor outcome. EHG interpretation consisted of fast Fourier transform (FFT) analysis. Of the 89 subjects who completed the study, 27% delivered preterm. While Doppler indices correlated well with outcome, the EHG interpretation method employed was less successful. Only the mean amplitude at 0.1-Hz differed between the groups, and then only at recordings between 31 and 34 weeks gestation.

Maner et al. (Predicting term and preterm delivery with transabdominal uterine electromyography. Obstet. Gynecol. 2003; 101: 1254-60) investigated 99 women (57 term and 42 preterm) presenting with complaint of contractions. They were monitored with two sets of bipolar electrodes for 30-minutes. FFT was performed on the electrical bursts identified in the signals and the power spectrum peak frequency compared using ROC analysis. They were able to predict, with positive predictive value (PPV) of 0.85, which term patients would deliver within 24 hours. For preterm patients, they predicted delivery within four days with PPV of 0.86. In addition, Garfield et al. (Comparing uterine electromyography activity of antepartum patients versus term labor patients. Am. J. Obstet. Gynecol. 2005; 193: 23-9) documented that the average power density spectrum peak frequency increases with advancing gestation, but increases significantly more during labor.

Prediction of uterine contractile strength is another area gaining attention. Maul et al, (Non-invasive transabdominal uterine electromyography correlates with the strength of intrauterine pressure and is predictive of labor and delivery. J. Matern. Fetal Neonatal Med. 2004; 15: 297-301) studied 13 patients with simultaneous IUPC monitoring. They integrated the active intrauterine pressure (above the baseline), and calculated the energy of the electrical bursts by 'multiplying the sum of the Y-values of the power density spectrum between 0.34 and 1.0 Hz by the duration of the electrical burst in seconds.' They found a strong correlation (r=0.764, p=0.002) between these and concluded that EHG accurately reflects uterine contractile activity.

Most of the work found in the literature exploits the time course of the EHG in one or at most a few channels. Relatively little investigation into the spatial organization of the uterine electrical activity has occurred. More than 50 years ago, Caldeyro et al. (A Better Understanding of Uterine Contractility through Simultaneous Recording with an Internal and a Seven Channel External Method. Surgery Gynecology & Obstetrics 1950; 91: 641-50) investigated spatial progression of uterine contractions. They placed both an internal sensor and seven external uterine activity monitors in 18 women in 'normal, prolonged, and false labors.' Though statistics are lacking, his group identified several factors that contributed to prolonged labors, the most important of which were absolute intensity of contractions and absence of fundal dominance.

Spatling et al. (External 4-Channel Tocography During Delivery. International Journal of Gynecology & Obstetrics 1994; 46: 291-5) performed four-channel tocography on 54 laboring patients (≥2 cm dilation) for 30-minutes. The four toco signals were plotted in parallel and the time differences in contraction onset between transducers determined by hand. They report that a right fundal onset of the contraction correlated with subsequent vaginal delivery: 2/30 women (7%) with predominant upper right origin of contractions were delivered abdominally, compared with 7/24 (29%) of women with predominance at other sites, p<0.05.

Using IUPC's placed in both the upper and lower uterine segments of laboring women, Margono et al. (Intrauterine Pressure Wave Characteristics of the Upper and Lower Uterine Segments in Parturients with Active-Phase Arrest. Obstetrics and Gynecology 1993; 81: 481-5) studied 15 patients with active phase labor arrest and seven with normal (non-augmented) labor. Mean active pressure was calculated for 12 contractions preceding oxytocin administration, and 12 during the maximal oxytocic effect. Comparisons were made between patients with arrest and those delivering spontaneously and, for the augmented patients, between those that delivered vaginally and those requiring cesarean. In every patient who delivered vaginally (either spontaneously (n=7) or with augmentation (n=9)), the fundal mean active pressure exceeded that of the lower segment. The opposite was true for the abdominally delivered women (n=6): in every patient, the lower segment mean active pressure exceeded that of the fundus both before and after oxytocin augmentation. Interestingly, oxytocin augmentation caused no significant change in the mean active pressure in either segment for either group. The authors note this fundal dominance 'might be used to gauge the likelihood of success of oxytocin augmentation.'

As noted above, uterine activity is currently monitored by tocodynamometer or IUPC, but neither correlates directly with progress of labor. No current method is effective in predicting labor success, and while serial cervical exams are the gold standard, repeated examinations are limited due to the potential for infection. Early diagnosis of failure to progress in labor will increase patient well-being, decrease hospital costs, and maximize system efficiency. Similarly, there is no reliable method of diagnosing real preterm labor. At present cervical examination is used, and sometimes transvaginal ultrasound or an expensive test of vaginal fluid (fetal fibronectin), but none has an adequate predictive value. A preterm labor detection method would (1) enable preparation for preterm delivery (betamethasone administration to mature lungs, transfer to a tertiary care center) as well as (2) allow those who are not in labor to be sent home sooner.

In summary, the majority of modern research into labor monitoring focuses on detecting intrapartum fetal asphyxia, which affects about 2% of all deliveries, and is the indication for about 10% of cesareans. See Farine D et al., The need for a new outlook on labor monitoring. Journal of Maternal-Fetal & Neonatal Medicine 2006; 19: 161-4. While clearly this research is valuable, a system to better manage labor itself would impact a much larger number of patients. There is a need for a non-invasive means of diagnosing preterm labor, determining labor progress, identifying labor arrest, monitoring response to oxytocin augmentation, accurately distinguishing arrest from very slow labor, and early identification of future labor dystocia. A reliable monitor with these features could improve outcomes of preterm deliveries, reduce the cesarean delivery rate (by identifying those labors that are merely slow), and shorten labor (by aiding in oxytocin titration and early administration, as well as identifying true arrest so cesarean delivery can proceed). The result would be improved patient satisfaction, reduced use of health-care resources, and reduced infectious complications (by reducing IUPC usage, frequency of cervical exams and labor duration).

BRIEF SUMMARY OF THE INVENTION

The subject invention provides systems and methods for dynamic uterine activity mapping, which is derived from a plurality of electrodes for assessing EHG that are placed on the maternal abdomen. The subject systems and methods uniquely analyze the spatio-temporal characteristics of the uterus and its effectiveness in labor.

In one embodiment, the subject invention utilizes spatio-temporal information provided from multiple electrodes (also referred to herein as EHG channels) to derive parameters that quantify efficient contractions. Contraction efficiency enables clinical assessment of various aspects of labor, including:

Progress of labor monitoring: the ability to track efficient versus inefficient contractions allows the clinician to know when a patient's labor is unlikely to progress to delivery. This early detection of failure to progress can save the hospital money, save the staff time and effort, and avoid problems that might be caused by prolonged attempts to deliver vaginally.

Effectiveness of labor augmentation: the ability to identify the need for oxytocin, and to rapidly assess its effect and speed its accurate titration, with a minimum of cervical exams, thus reducing the risk of chorioamnionitis Transition during labor induction: the ability to recognize when a misoprostil or other induction is ready for oxytocin, limiting cervical exams and speeding inductions by avoiding unnecessary delays.

Preterm labor monitoring: many patients arrive at the hospital with preterm labor symptoms. Today, there is not a clear method of determining whether the patient is actually in preterm labor or not. This invention may be used to rapidly triage patients and send home those patients who are not in preterm labor.

Home monitoring: either similar to the above discussion for continuous preterm labor monitoring at home, or for parents who would like a better indication of when they should leave for the hospital (e.g. to discriminate between real labor and false labor).

External IUP prediction: EHG cannot currently replicate the performance of internal monitoring of uterine pressure (IUPC). With an appropriate understanding of the electrical characteristics of the EHG, a non-invasive method of predicting IUP within a certain range is possible. Thus replacing the role of the IUPC in determining the adequacy of contractions.

Detection of elevated baseline uterine tone and uterine rupture. The subject invention can predict and detect problems with overall uterine activity.

Patient feedback on effective methods of 'pushing'

With the subject invention, muscle electrical activity is measured externally Uterine contractions are the result of the coordinated actions of individual myometrial cells. At the cellular level, the contractions are triggered by a voltage signal called an action potential. The local action potentials during uterine contractions can be measured with electrodes placed on the maternal abdomen resulting in a uterine EMG signal (hereinafter referred to as "EHG": electrohysterogram).

The EHG provides contraction frequency and duration information of the myometrium only in the vicinity of the electrode. Extraction of EHG data has existed in the literature for many years. This invention specifically relates to the extraction of information concerning the coordination and spatio-temporal patterns of uterine contractions that can be captured by collecting multiple channels of EHG. A single lead EHG (or an external tocodynamometer, which is currently used), will not be able to quantify tonus, nor fundal dominance, nor the complex movement of the contraction throughout the uterus. The subject invention uniquely finds useful information in the spatio-temporal relationship between the EHG signals and also provides methods of quantifying these relationships. For example, fundal dominance and spatial co-ordination of the contraction can only be ascertained with multiple electrodes placed over the uterus.

In a preferred embodiment of the invention, electrohysterographic information is used in the diagnosis and management of normal and abnormal labor, in particular dystocia. According to the subject invention, spatio-temporal pattern changes detected by EHG can produce short-term predictions of dilation, while predominance of certain patterns correlate with eventual dystocia. The subject invention provides a contraction efficiency indicator that estimates the dilation at the next cervical exam (short term evaluation) as well as a dystocia prediction indicator that estimates the likelihood of eventual vaginal delivery or a preterm delivery.

Specifically, the subject invention provides a model that predicts labor progress. The model can be used to establish a contraction efficiency indicator. According to the subject invention, regions of data from arrested patients before and after oxytocin augmentation can be utilized to establish parameters that are significantly different between periods of pre-arrest, positive oxytocin response, and lack of oxytocin response. Models, composed of the parameters shown to correlate with the short-term ability of the contractions to produce dilation, are created and analyzed to determine the ability of the models to predict if the patient is currently dilating adequately.

In another embodiment, a model is provided that predicts labor outcome. This model can be used to establish a dystocia prediction indicator. According to the subject invention, parameterization of spatio-temporal EHG activity is evaluated to determine which parameters are significantly different in normal labor and dystocia/dysfunctional labor cohorts. The features that indicate the long-term success of labor are utilized in models to estimate the likelihood of labor dystocia.

The systems and methods of the invention provide key insights into the physiology of the uterine electrical activity and its long- and short-term effects on the laboring patient. In particular, the subject invention provides the clinician with the ability to recognize labor abnormalities, manage and monitor labor augmentation, and identify true labor arrest. Benefits of the invention include (1) more accurate and earlier recognition of labor dystocia; (2) more accurate oxytocin titration; (3) reduced infectious complications from a reduction in IUPC placement, need for serial cervical examinations, and perhaps earlier termination of doomed labor attempts; (4) perhaps reduced cesarean deliveries for dystocia by distinguishing slow labor from genuine arrest; (5) improved patient satisfaction and comfort and reduced resource utilization for failed labors; (6) perhaps improved prediction of success of labor induction; and (7) prediction of preterm delivery

BRIEF DESCRIPTION OF DRAWINGS

The file of this patent contains at least one drawing executed in color. Copies of this patent with color drawings(s) will be provided by the Patent and Trademark Office upon request and payment of the necessary fee.

FIG. 15 is a table illustrating the pairing of patient demographics and delivery variables.

DETAILED DISCLOSURE

Figure 1A:
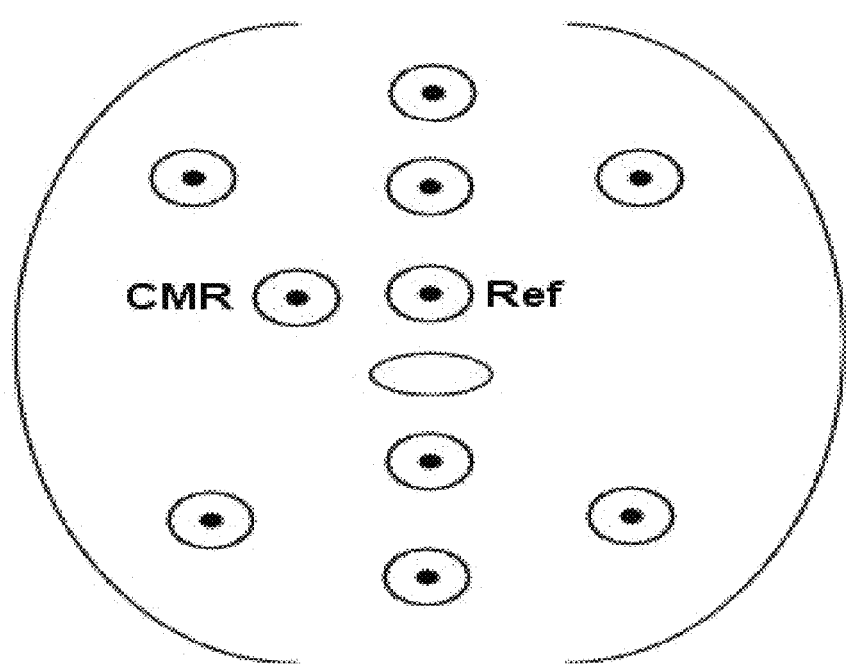
FIG. 1A illustrates a set of electrodes positioned on a maternal abdomen in accordance with the subject invention.

The subject invention provides systems and methods for non-invasive, comprehensive monitoring of uterine contractile activity using uterine EMG signals (also referred to herein as "EHG"). In one embodiment, the systems and methods of the invention enable quantification of uterus contraction for use in monitoring the progress of labor as well as predicting labor success and diagnosing real preterm labor. In a related embodiment, data regarding uterus contraction activity is extrapolated to offer support/advice in making clinical decisions.

In one embodiment, the system comprises (1) a plurality of surface sensors for extraction of EHG signals; (2) a data storage device for collecting sensor input; (3) a computing means for receiving and analyzing the spatio-temporal information in the sensor input to extract EHG results and derive parameters, including without limitation, time of contraction, location of contraction, extent of contraction, direction of propagation (gradient), speed of propagation over the abdomen, average contraction over time, spatial location of the peak of contraction and its variance, spread of the contraction, abdominal intensity distribution, abdominal frequency distribution, patterns of intensity over time, distance of peak power propagation, power changes over time, frequency changes over time; and using the parameters to quantify uterine contraction (i.e., to establish a contractile map of the uterus (COMU)) and for clinical use in monitoring progress of labor, monitoring preterm labor, remote or home monitoring of preterm labor, external IUPC prediction, and pharmaceutical efficacy (i.e., titration of oxytocin). A graphical user interface can be included with the systems of the invention to display clinical data as well as enable user-interaction.

In one embodiment, the system of the invention further includes an intelligence system that can use the parameter data generated by the processor in offering support/advice for making clinical decisions (i.e., to interpret labor progress, likelihood of delivery within a period of time; and likelihood of successful vaginal delivery). An intelligence system of the subject invention can include, but is not limited to, artificial neural networks, fuzzy logic, evolutionary computation, knowledge-based systems, optimal linear or nonlinear filtering, and artificial intelligence.

In one embodiment, a neural network system is provided in the monitoring system of the invention to enable real-time assistance in providing additional clinical data (i.e., classification of labor progress and prediction of preterm labor).

In accordance with the subject invention, the computing means is preferably a digital signal processor, which can (1) automatically, accurately, and in real-time, extract EHG signals from sensor input; (2) process EHG signals into parameters useful in assessing uterine contraction; (3) determine contraction efficiency for use in monitoring progress of labor, monitoring preterm labor, and external IUPC prediction.

In one embodiment, the system of the subject invention is stationary. For example, the system of the invention can be used within a healthcare setting (i.e., hospital, physician's office).

In another embodiment, the system of the subject invention is portable for use outside of a healthcare setting (i.e., home use). In a related embodiment, a portable system enables continuous non-invasive uterus monitoring for beneficial assessment of labor (i.e., presence of effective contraction to determine labor). Such monitoring can provide information not only to the user (i.e., mother) but also provide off-site information to the healthcare provider. For example, continuous monitoring can be accomplished remotely from the location of mother/fetus by the healthcare provider.

Sensors

In accordance with the subject invention, EHG signals are extracted in real time using sensors that do not endanger fetal health. In a preferred embodiment, a set of electrodes is used to sense EHG signals.

One embodiment of the invention utilizes a set of electrodes (at least 4 electrodes but preferably 6 up to 200 electrodes) provided on a mesh (or vest), wherein the mesh can function as an electrode-stabilization component. Such a mesh can be prepared using any suitable material that permits the mesh to be both lightweight and comfortable. The benefits of a system of this type are the ease of use and reduction of preparation time required to appropriately place the electrodes on a patient. For example, preparation time can be reduced from 15-30 minutes for adhesive-based disposable electrodes to about 5 minutes using a mesh of the invention. In addition, a mesh of electrodes according to the subject invention permits consistent (and repeatable) extraction of maternal-fetal vital signs.

1. Signal Data Collection

Figure 1B:
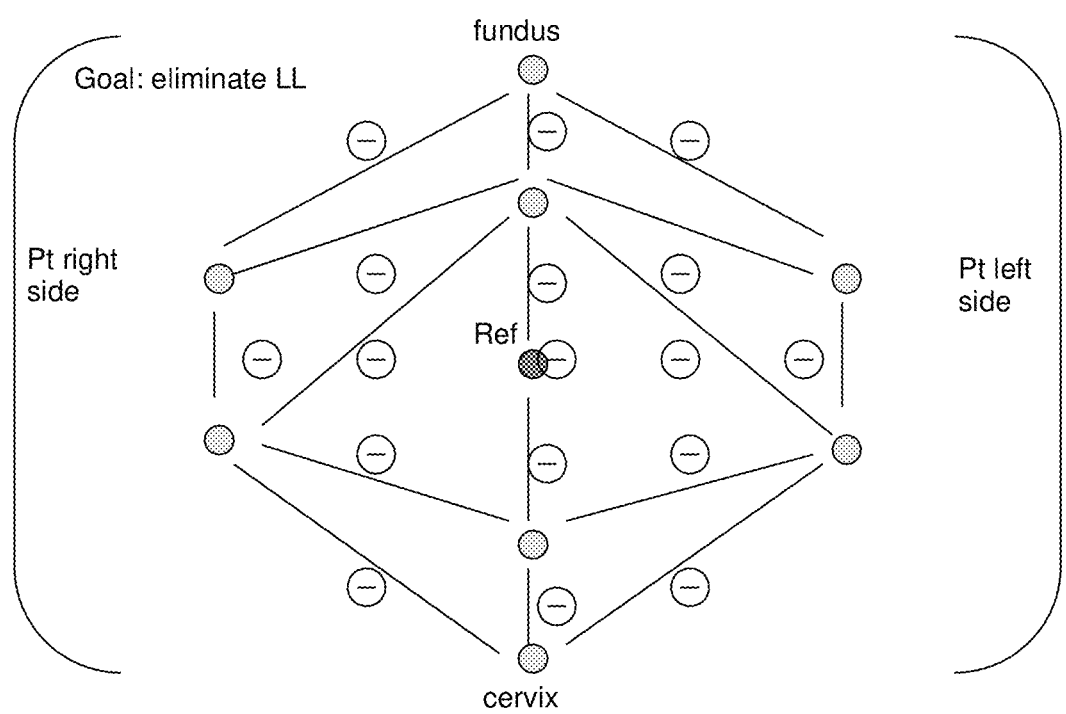
FIG. 1B illustrates signals generated by pair-wise subtraction at various locations over the maternal abdomen.

In the preferred embodiment, EHG signals are collected with electrodes referenced to the center of the abdomen (See FIGS. 1A and 1B; center of the abdomen referenced as 'Ref' in the figures). Preferably, abdominal skin is prepared by gentle rubbing with abrasive gel. Following skin preparation, electrodes (i.e., ten 3-cm$^2$ Ag/AgCl$_2$ electrodes, Ambu; Glen Burnie, Md., USA) are positioned on the maternal abdomen as shown in FIG. 1A.

In one embodiment, the electrodes are connected to an amplifier in a monopolar fashion with centrally located common reference and common mode rejection leads. Electrode positions can be modified slightly for each patient, as required by the location of a tocodynamometer and ultrasound fetal heart rate monitor, if present. Impedance of each electrode is then measured (as compared with the reference) (General Devices EIM-105 Prep-Check; Ridgefield, N.J., USA). Skin preparation can be repeated as needed at each site until the measured impedance is below 10 kΩ, where possible. In a preferred embodiment, eight electrodes are used.

In one embodiment, recorded EHG signals are fed to a high resolution, low-noise amplifier. Where eight electrodes are used, the eight recorded EHG signals are fed to an 8-channel high resolution, low-noise unipolar amplifier with a wide dynamic range. All eight signals are measured with respect to the reference electrode. The amplifier 3 dB bandwidth is preferably from about 0.01 to about 10 Hz. According to the subject invention, the EHG signal data can be digitized for processing (e.g. transferred to a personal computer via a 16-bit resolution A/D card). In certain embodiments, data from a standard maternal-fetal monitor (such as Corometrics, GE Medical Systems) can also be collected for comparison.

In a preferred embodiment, 15 signals are created from the 8 signals generated from the electrodes, where the 15 signals are provided by pairwise subtraction between electrode neighbors to subtract the commonality of the reference and providing local information about the uterus contractility pattern. These 15 signals plus two of the original EHG channels represent the local contraction strength on 17 locations over the abdomen (see FIG. 1B). Potentially more channels can be used for a wider coverage with higher spatial resolution.

Amplifier

As noted above, an amplifier can be used to amplify EHG signals collected by the set of sensors of the invention. Amplifiers for use in the collection of EHG signals are known in the art. In one embodiment, the amplifier of the invention is a high-resolution, low-noise, unipolar amplifier (i.e., all channels of signals are referenced from a single electrode). In a preferred embodiment, a driven right leg (DRL) circuit is utilized to actively suppress noise and improve the common mode rejection ratio (CMRR) of the amplifier.

Figure 11:
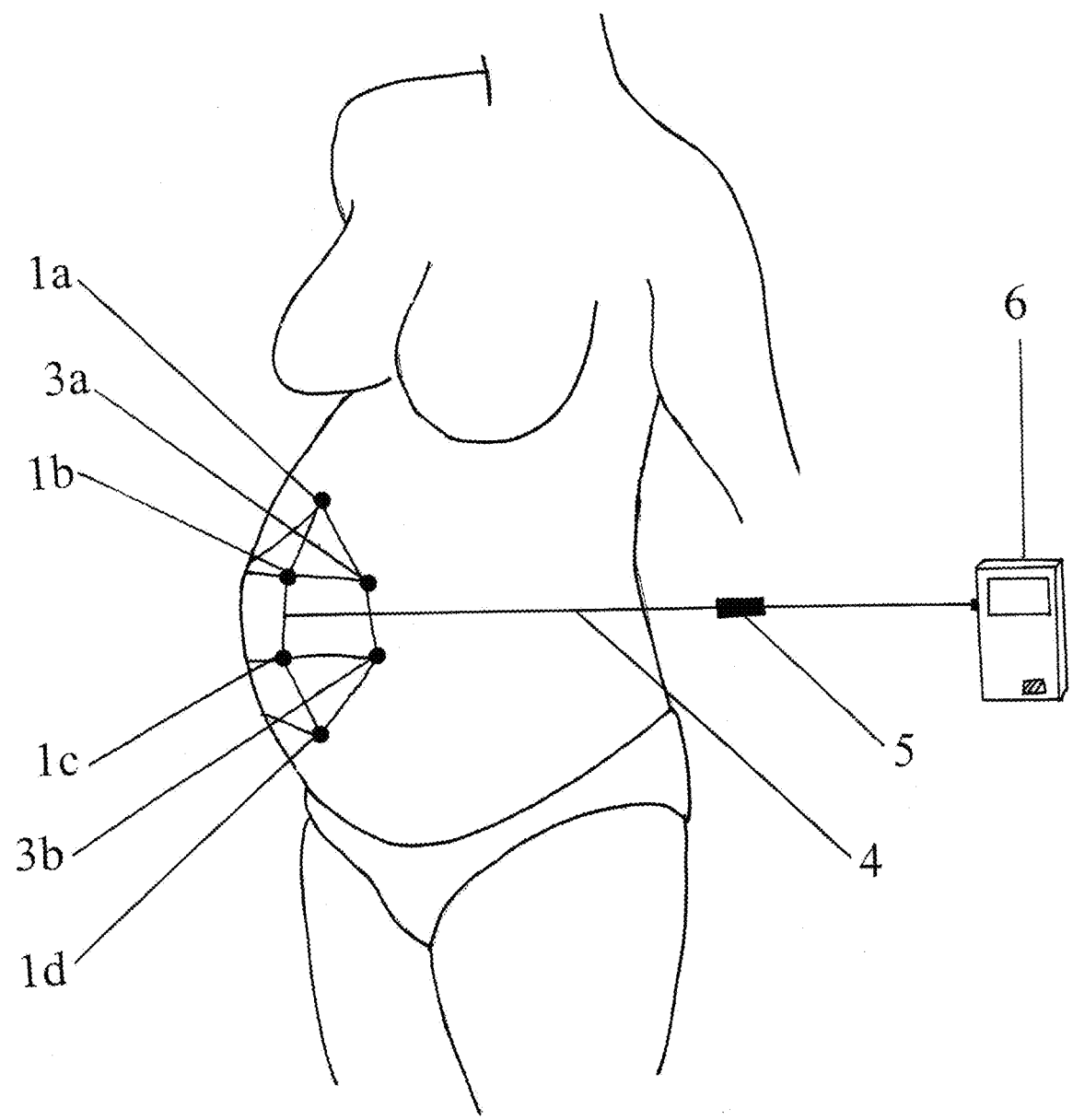
FIG. 11 illustrates one embodiment of the maternal-fetal monitoring system, wherein the monitoring system is ambulatory.

In another embodiment, as illustrated in FIG. 11, the amplifier 5 has a 15-pin D-sub connector that interfaces with an electrode cable 4 connected to a set of electrodes 1a-d, 3a-b. Preferably, the electrode cable is a 10-lead shielded ECG cable. A shielded cable is essential to reduce any noise interference due to frequencies from various power sources. But other means of providing shielding such as fiber optical cables are preferred. In one embodiment, amplifier output can interface to an analog-to-digital converter (A/D) converter. A power supply is provided to operate the amplifier. Preferably, the power supply includes an adapter that is a 12V AC-DC medical grade power supply adapter and a power converter, which is provided to protect the patient from leakage currents.

The A/D converter can be situated in the amplifier or in a computing means 6 of the invention. An A/D converter can be selected from a variety of suitable types known in the art that have the desired dynamic input range. A/D converters encode sensor signals for respective sensor channels into a digital format, such as a 16 bit format, at a desired sampling rate, such as 10 Hz.

Filters

According to the subject invention, at least one filter can be included in the contraction/labor progress monitoring system. Filters of the invention can be applied to sensor signals prior to processing, during processing, or post processing as performed in the computing means; or some combination thereof. In certain embodiments, the filter(s) are applied at the amplifier to signals communicated from the sensors, prior to any processing performed by the computing means. In a related embodiment, filters are also applied to signals during and after processing by the computing means (i.e., filters applied prior to and during parameter extrapolation operations). In certain embodiments, linear or non-linear filtering is performed by an intelligence system of the subject invention.

Filters of the invention can be analog filters, such as those used for suppressing specific frequency components, which are well known in the art. Further, digital filters are also contemplated for use in the subject monitoring system. In certain embodiments, digital filtering operations are accomplished using a computing means, preferably a computer processor (i.e., microprocessor or digital signal processor (DSP)).

By using filter(s), important signal components can be easily examined by filtering out undesired spectral components such as noise. According to the subject invention, filtering operations that can be used, either alone or in combination, in extracting vital signal components include, but are not limited to, finite impulse response (FIR) filters and infinite impulse response (IIR) filters, such as band-pass filters, high pass filters, low pass filters, band-stop (or "notch") filters, and also to non-linear filters such as the median filter.

In certain embodiments, at least one band pass filter and/or low pass filter is applied to EHG signals prior to processing with parameter calculations operations.

In a preferred embodiment, the low pass filter is a Butterworth filter. When a band pass filter is applied, the cut-off frequency is 10 Hz. Most preferably, a combination of band pass filter(s) is applied to vital signals, wherein the pass band is 0.01 Hz and 10 Hz.

Hardware

EHG signals obtained in accordance with the subject invention are transmitted from the sensors to a computing means for signal processing. The computing means can also be responsible for maintenance of acquired data as well as the maintenance of the contraction/labor progress monitoring system itself. The computing means can also detect and act upon user input via user interface means known to the skilled artisan (i.e., keyboard, interactive graphical monitors).

In one embodiment, the computing means further comprises means for storing and means for outputting processed data. The computing means includes any digital instrumentation capable of processing signals from the sensors of the invention (i.e., EHG signals). Such digital instrumentation, as understood by the skilled artisan, can process communicated signals by applying algorithm and filter operations of the subject invention. Preferably, the digital instrumentation is a microprocessor, digital signal processor (DSP), a personal desktop computer, a laptop, and/or a portable palm device. The computing means can be general purpose or application specific.

The subject invention can be practiced in a variety of situations. The computing means can directly or remotely connect to a central office or health care center. In one embodiment, the subject invention is practiced directly in an office or hospital. In another embodiment, the subject invention is practiced in a remote setting, for example, personal residences, mobile clinics, vessels at sea, rural villages and towns without direct access to healthcare, and ambulances, wherein the patient is located some distance from the physician.

In a related embodiment, the computing means is a custom, portable design and can be carried or attached to the patient in a manner similar to other portable electronic devices such as a portable radio, or interwoven in the patient clothing as a wearable computer.

Figure 12:
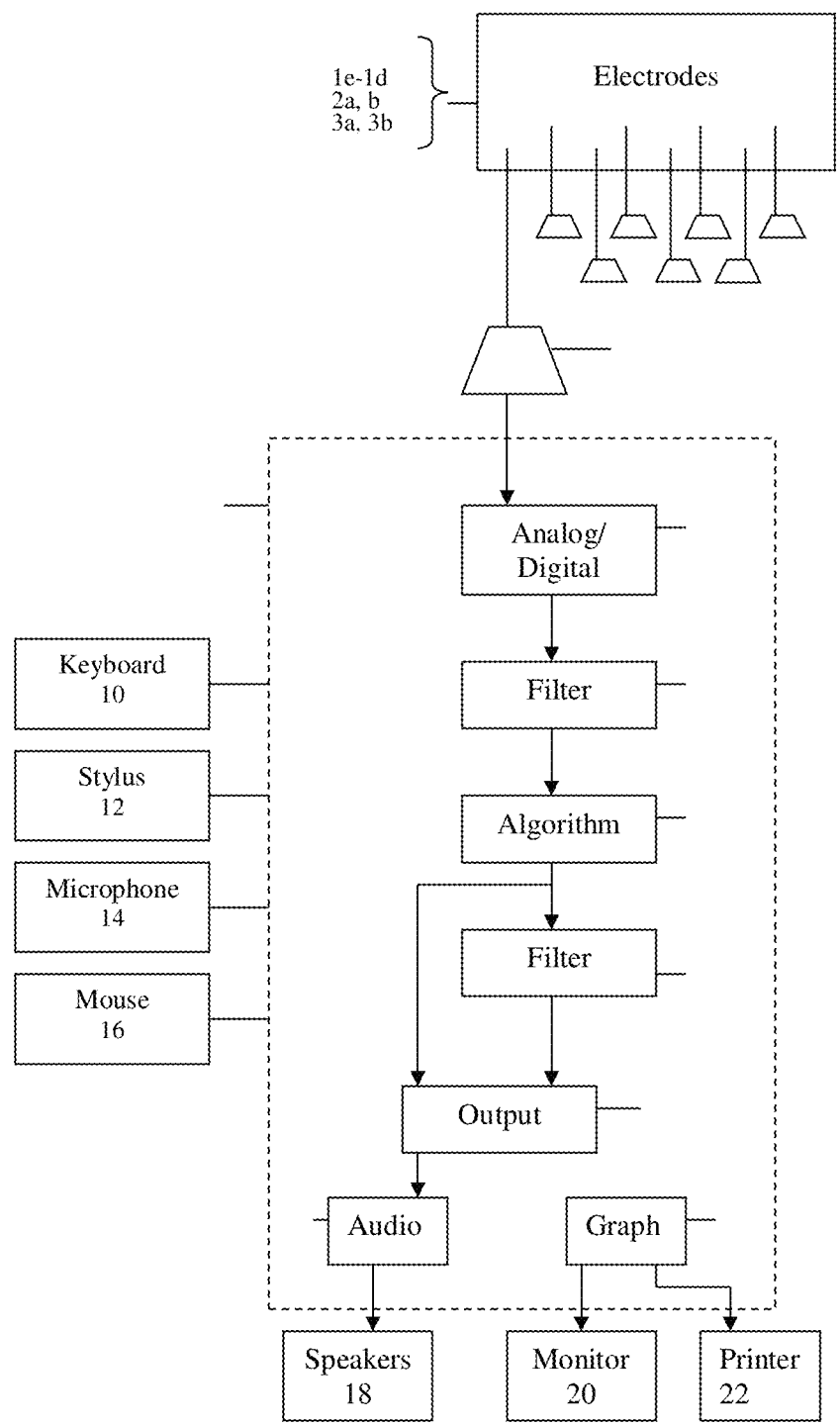
FIG. 12 illustrates a computing means used in accordance with the subject invention.

Referring to FIG. 12, the computing means used in accordance with the subject invention can contain at least one user-interface device including, but not limited to, a keyboard 10, stylus 12, microphone 14, mouse 16, speaker 18, monitor 20, and printer 22. Additional user-interface devices contemplated herein include touch screens, strip recorders, joysticks, and rollerballs.

Preferably, the computing means comprises a central processing unit (CPU) 30 having sufficient processing power to perform algorithm operations in accordance with the subject invention. The algorithm operations 36, including the filtering operations 34 and 38, can be embodied in the form of computer processor usable media, such as floppy diskettes, CD-ROMS, zip drives, non-volatile memory, or any other computer-readable storage medium, wherein the computer program code is loaded into and executed by the computing means. Optionally, the operational algorithms of the subject invention can be programmed directly onto the CPU using any appropriate programming language, preferably using the C programming language.

In certain embodiments, the computing means comprises a memory capacity sufficiently large to perform algorithm operations in accordance with the subject invention. The memory capacity of the invention can support loading a computer program code via a computer-readable storage media, wherein the program contains the source code to perform the operational algorithms 36 of the subject invention. Optionally, the memory capacity can support directly programming the CPU to perform the operational algorithms of the subject invention. A standard bus configuration can transmit data between the CPU, memory, ports and any communication devices.

In addition, as understood by the skilled artisan, the memory capacity of the computing means can be expanded with additional hardware and with saving data directly onto external mediums including, for example, without limitation, floppy diskettes, zip drives, non-volatile memory and CD-ROMs.

As described above, the computing means can include an A/D converter to translate analog signals into digital signals 32 (i.e., an analog/digital card). The A/D converter preferably readies the signals for further processing according to the subject invention. Additional filtering steps may precede any algorithmic operations of the invention.

The computing means can further include the necessary hardware and software to convert processed signals into an output form 40 readily accessible by the trained physician, nurse practitioner, midwife, or technician. For example, without limitation, an audio device 42 in conjunction with audio speakers 18 can convert and play a processed uterine information into an audio signal, and/or a graphical interface 44 can display ECG signals in a graphical form on a monitor 20 and/or printer 22. Further, the computing means can also include the necessary software and hardware to receive, route and transfer data to a remote location or to an existing fetal monitoring system.

In one embodiment, the patient is hospitalized, and clinical data generated by a computing means is transmitted to a central location, for example, a monitoring station located in a maternity ward, or to a specialized physician located in a different locale.

In another embodiment, the patient is in remote communication with the health care provider. For example, patients can be located at personal residences, mobile clinics, vessels at sea, rural villages and towns without direct access to healthcare, and ambulances, and by using the contraction/labor progress monitoring system of the invention, still provide clinical data to the health care provider. Advantageously, mobile stations, such as ambulances, and mobile clinics, can monitor maternal-fetal health by using a portable computing means of the subject invention when transporting and/or treating a patient.

To ensure patient privacy, security measures, such as encryption software and firewalls, can be employed. Optionally, clinical data can be transmitted as unprocessed or "raw" signal(s) and/or as processed signal(s). Advantageously, transmitting raw signals allows any software upgrades to occur at the remote location where a computing means is located. In addition, both historical clinical data and real-time clinical data can be transmitted.

Communication devices such as wireless interfaces, cable modems, satellite links, microwave relays, and traditional telephonic modems can transfer clinical data from a computing means to a healthcare provider via a network. Networks available for transmission of clinical data include, but are not limited to, local area networks, intranets and the open internet. A browser interface, for example, Firefox or INTERNET EXPLORER, can be incorporated into communications software to view the transmitted data.

Advantageously, a browser or network interface is incorporated into the processing device to allow the user to view the processed data in a graphical user interface device, for example, a monitor. The results of algorithm operations of the subject invention can be displayed in the form of the interactive graphics, such as those illustrated in FIGS. 4A-4F. The user, whether it be a physician, a nurse, a technician, or a patient, can indicate the placement of the electrodes on the graphical maternal abdomen. In one embodiment, a graphical representation of the maternal abdomen is provided (see FIG. 1A) to track the location of the sensors (i.e., electrodes) as well as to indicate to the user whether optimal EHG signals are being detected by the sensors.

Software

Figure 13:
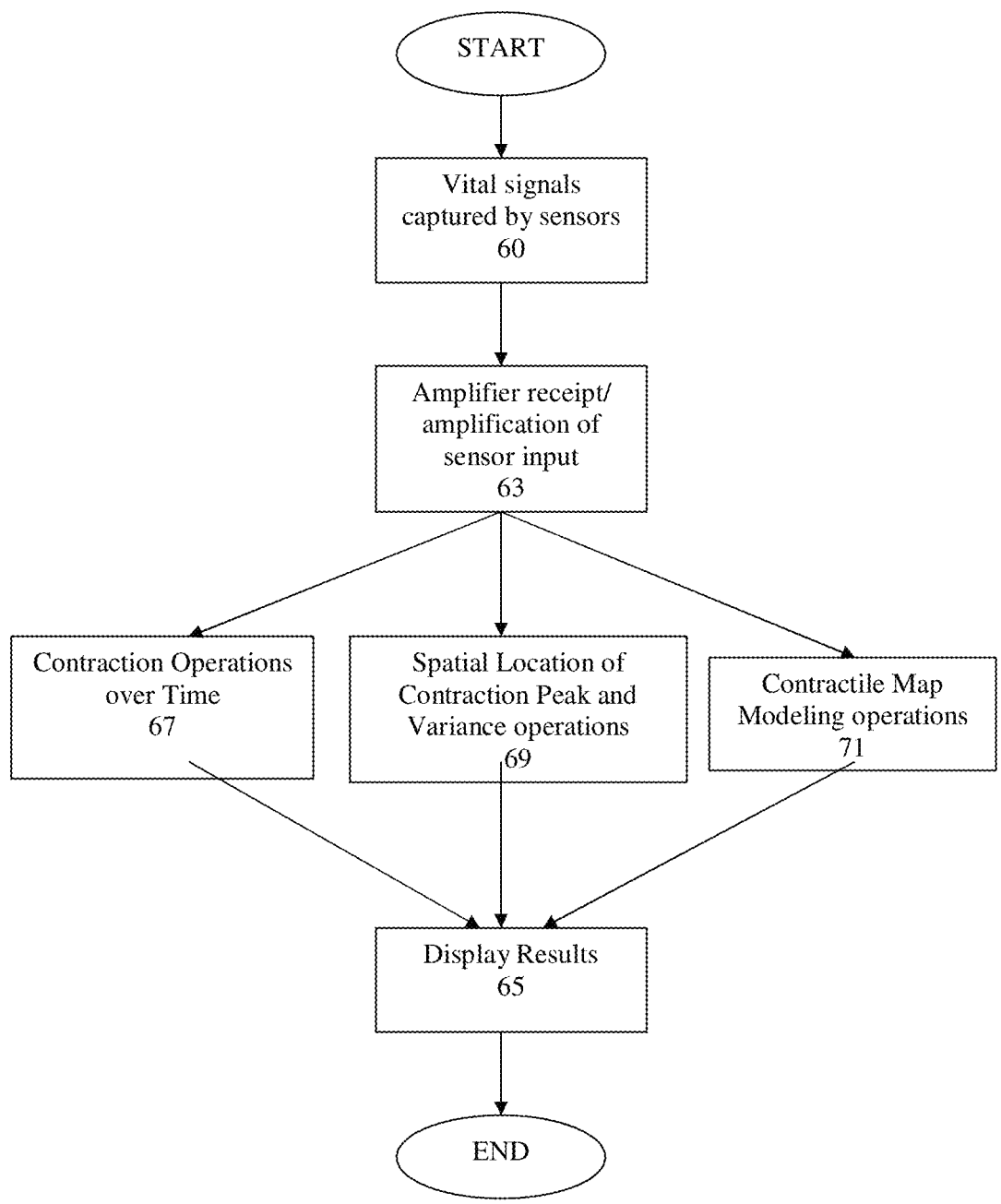
FIG. 13 illustrates a flow diagram illustrating steps for operating a maternal-fetal monitoring system of the invention.

The contraction/labor progress monitoring system of the subject invention can function in a real-time setting to continuously provide accurate clinical data to the user. In operation, as illustrated in FIG. 13, EHG signals (raw signals) are captured by sensors 60 and input to an amplifier 63. Amplifier output is subsequently communicated to a variety of operational algorithms 36 for processing EHG signals into parameters for establishing clinical data (i.e., progress of labor, preterm labor, IUPC prediction, etc.) and subsequent presentation of clinical data to the user 65. Operational algorithms 36 can include, without limitation, average contraction over time operations 67, spatial location of contraction peak and variance operations 69, and contractile map modeling operations 71.

In certain instances, prior to EHG signal processing, signals received from an amplifier are communicated to filter operations for each sensor channel Raw signals extracted by sensors of the invention are a mixture of several sources, namely maternal-fetal vitals signs (i.e., maternal ECG, fetal ECG, EMG signals) and noise. In a preferred embodiment, each sensor channel is communicated to a corresponding band pass filter operation, which is accomplished on a computing means. According to one embodiment of the subject invention, a computer processor is used for filter operations as well as other processing functions.

In accordance with the subject invention, the filtered signals are then followed by appropriate operations for obtaining desired parameters (i.e., EHG results) for use in generating useful clinical data (such as progress of labor, preterm labor, IUPC prediction). Contemplated operations include, but are not limited to, EHG extraction operations; contractile map extraction operations, average contraction over time operations, spatial location of contraction peak and variance operations, and contractile map modeling operations.

1. EHG Extraction Operations

In one embodiment, a first signal processing step of the subject invention comprises communicating EHG signals to a computing means (such as a computer processor) for performing EHG extraction operations. Alternatively, certain embodiments of the invention do not require communication of EHG signals to a computing means.

EHG extraction operations are preferably implemented in real time. EHG extraction operations normalize over time each of the signal channels (from each sensor) by subtracting the mean and dividing by the standard deviation. Effectively, this creates EHG signals with unit variance and zero mean, according to the following equation:

$$y_i = (x_1 - \text{mean}(x_i))/\text{var}(x_i) \ i=1, \ldots, 17$$

Figure 2:
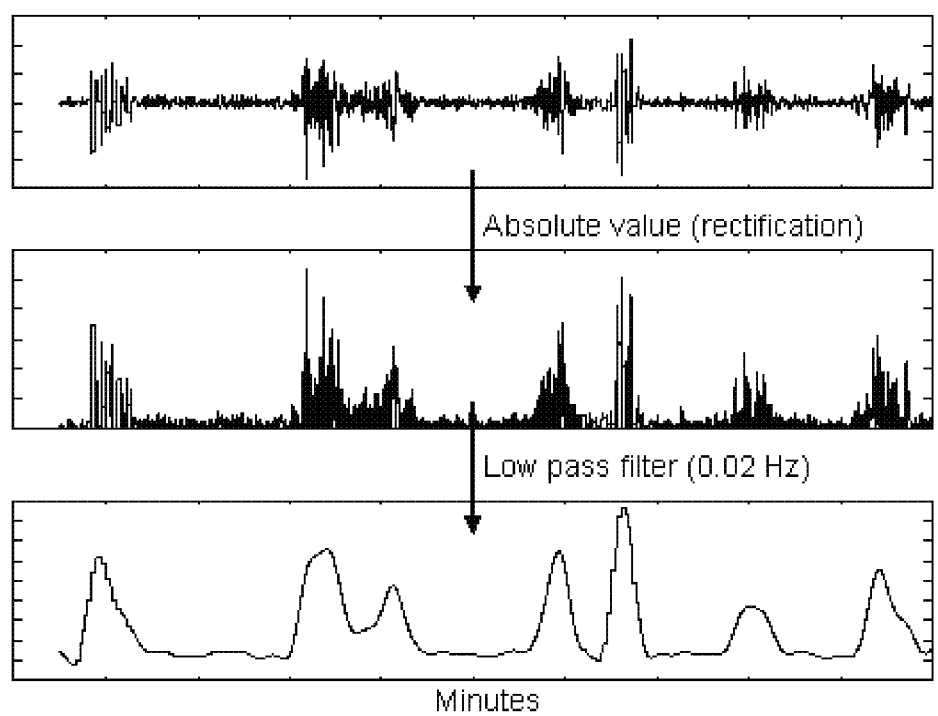
FIG. 2 illustrates contraction envelope processing (rectification and filtration) from one EHG channel performed in accordance with the subject invention.

These EHG signals are further processed to obtain their envelope. The absolute value is computed and passed by a lowpass filter (such as a $4^{th}$ order Butterworth lowpass filter) with a cutoff at 0.025 Hz (see FIG. 2):

$$z_i = LP\text{filter}(|y_i|) \ i=1, \ldots, 17$$

Such EHG signals can be further processed in accordance with methods known in the art to predict IUP. In one embodiment, optimal linear filtering is applied to extracted EHG signals of the invention to predict IUP. Preferably, a Wiener filter is used to predict IUP from EHG signals. In another embodiment, IUP is predicted using Montevideo units (MVU) that are calculated using the EHG signals extracted in accordance with the subject invention. Accordingly, the extracted EHG signals of the invention (and corresponding IUP predictions) provide contraction pattern and intensity information useful to the clinician. The predicted IUP is especially advantageous in the obese population where tocodynamometer data is normally not as accurate in detecting contractions.

2. Contractile Map Extraction Operations

In accordance with the subject invention, at the output of EHG extraction operations, contractile map extraction operations can be performed on a computing means (such as a computer processor), preferably in real time. The contractile maps provided by these operations are preferably spatio-temporal contractility maps that contain clinical information.

In one embodiment, from the EHG signals, location signals are generated by pair-wise subtraction between signal neighbors to remove common signal characteristics and provide local information about the uterine contractility pattern. These signals, plus other possible combinations of the EHG signals including the original EHG channels, represent the local contraction strength at various locations over the abdomen (FIG. 1B). Following generation of local information about the uterine contractility pattern, EHG extraction operations can then be performed.

Figure 5:
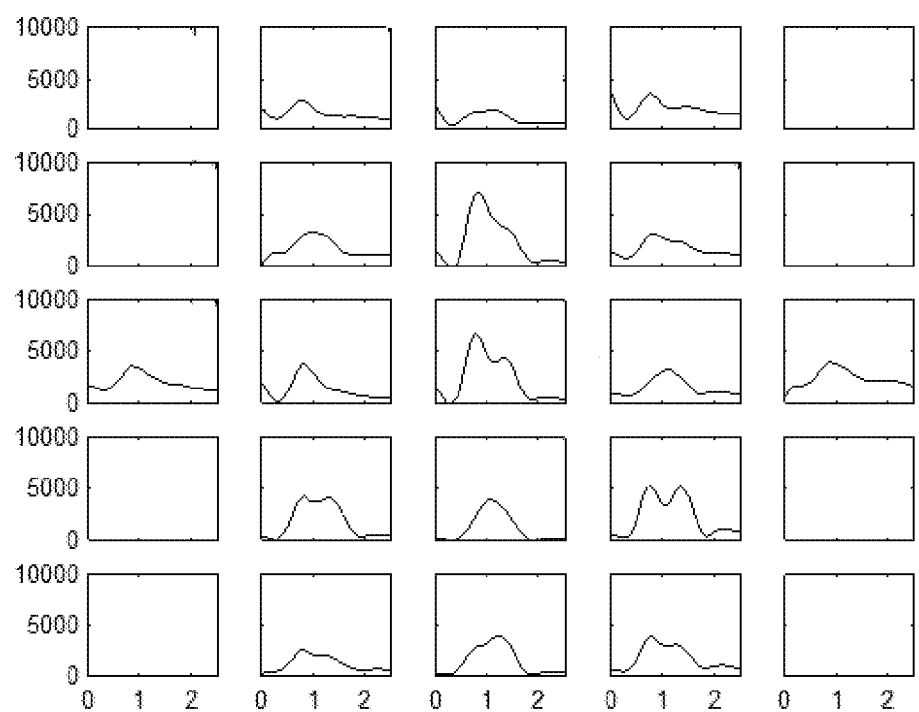
FIG. 5 illustrates envelopes of each contraction curve after rectification and filtration of the signals presented in FIG. 4.

Following derivation of the location signals, the spatio-temporal patterns of these location signals are displayed in a grid for a specified amount of time, preferably a 5×5 grid, 10 times a second. These grids can be interpolated over the abdomen and over time and displayed as a real time movie to the attending clinician and/or nurse. This movie contains a contractile map of the uterus (COMU). The creation of an example COMU is shown in FIGS. 3, 5, and 6.

Figure 3:
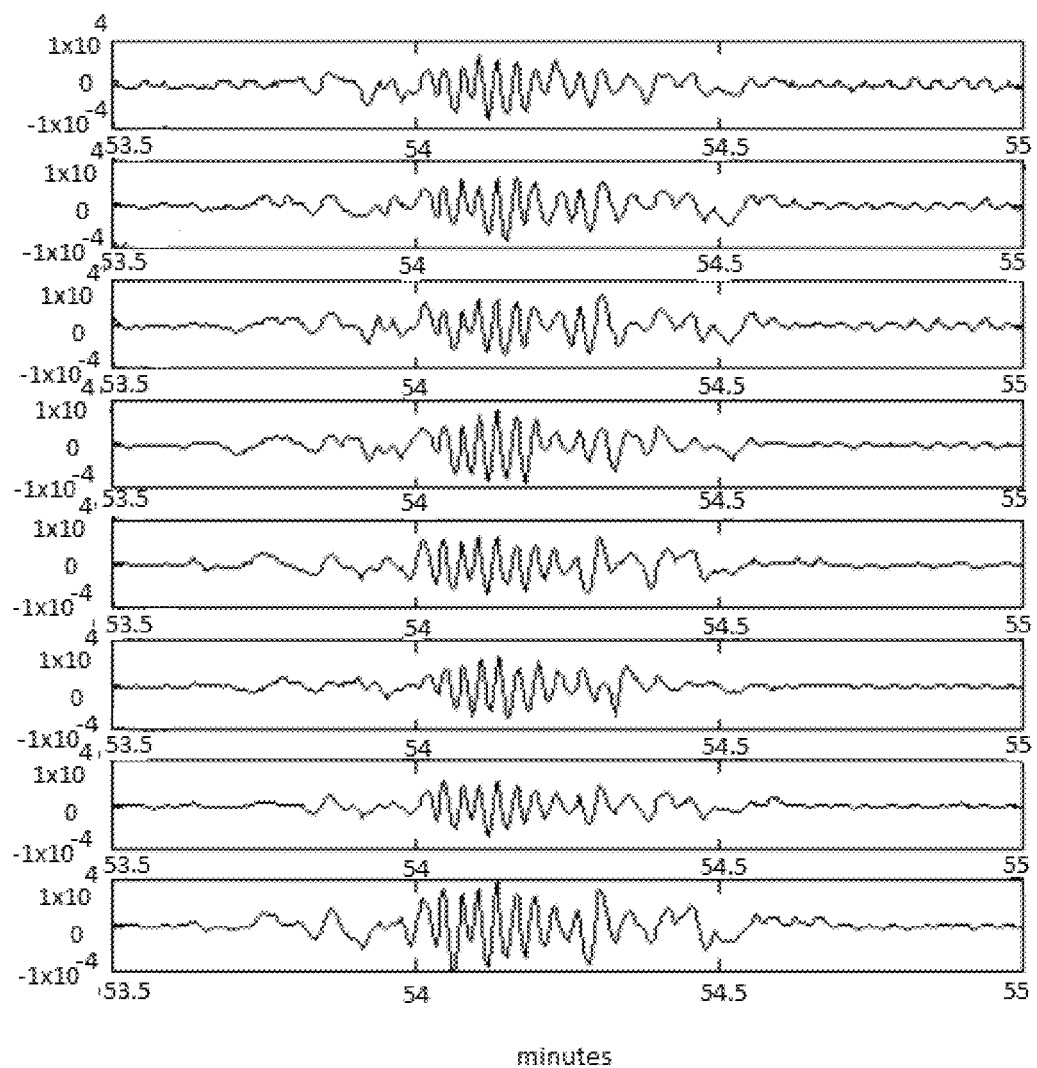
FIG. 3 illustrates EHG channels referenced to the umbilicus collected during one contraction in accordance with the subject invention.
Figure 4:
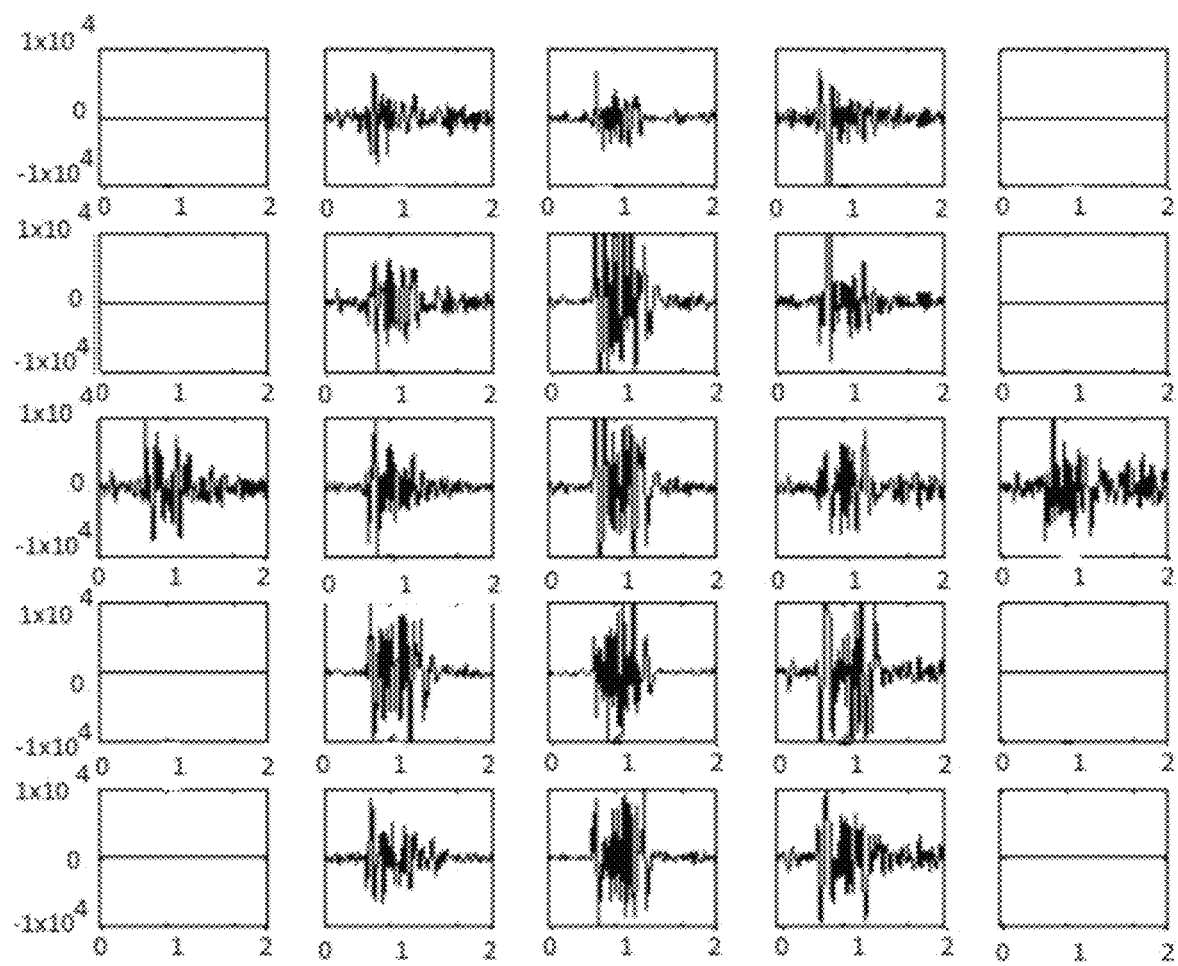
FIG. 4 represents signals generated after pairwise subtraction of the EHG signals presented in FIG. 3.

FIG. 3 shows 8 EHG channels referenced to the umbilicus collected during labor. Pairwise subtractions produces the signals in FIG. 4. According to the subject invention, the spatial variability that is obtained by pairwise subtraction emphasizes the local contractility of the uterus over the respective electrode. After rectification and filtering, as explained above, envelopes of each contraction curve are derived (see FIG. 5), where each envelope details striking differences in the timing and amplitude of the EHG signals at each location on the abdomen. At each time the value of the envelope is measured and placed on a grid of locations corresponding to the electrode placement over the uterus (such as a 5×5 grid). Such grids can be used to create, through interpolation, contour plots of the contractile map, color coded (red high, blue low), as illustrated in FIG. 6. The movie frame of FIG. 6 corresponds to an instant near the peak of the contraction, denoted by the arrows in FIGS. 3 and 5. The higher power region near the top of the map indicates fundal dominance.

Figure 6:
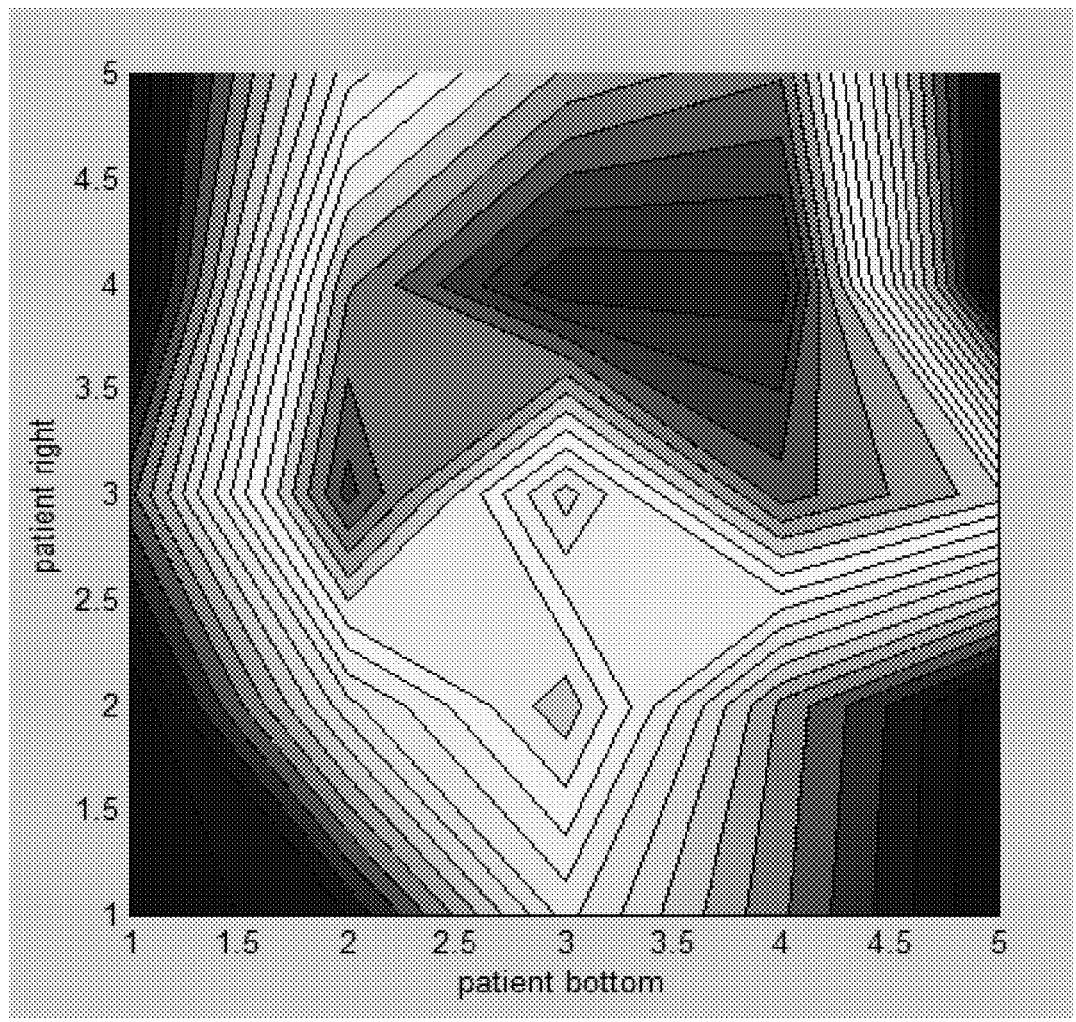
FIG. 6 is a snapshot of the contractile map of the uterus (COMU), which is a colorized image of the spatial contraction intensity over time, at a time t recorded during contraction where red corresponds to high power and blue to low power.

The COMU illustrated in FIG. 6 provides information about the patterns of contraction, i.e. when (in time) and where (in space) the contraction starts, it also provides information about the extent, the direction of propagation (gradient), the spread and the speed of propagation over the abdomen. In accordance with the subject invention, the contractile map provided by the subject invention can quantify fundal dominance and it is predicative of progress of labor. Furthermore, it can be visually evaluated by the attending physician and/or nurse.

The COMU provided in accordance with the invention contains unique information about the patterns of uterine electrical activity. For example, a COMU of the invention can estimate the center of a contraction by a calculation similar to the center of mass (see section 5 below) and the power (see section 4 below) as specified later. Alternatively, other models, such as Gaussian approximations or the like, can be used to estimate the center of a contraction. Further, a contractile map of the invention enables the quantification of a variety of parameters, such as fundal dominance, that can be predictive of effective contractions and progress of labor.

3. Extraction of Parameters from the COMU

According to the subject invention, a variety of parameters can be extracted from the COMU to further quantify the spatio-temporal uterine contractions by a computing means (such as a computer processor), preferably in real time.

The COMU is a visualization tool. Various parameters can be extracted from a COMU for automatic (such as computer-based operations) processing of the information. In one embodiment, the electrical activity of the uterus is modeled with a two-dimensional function (the contractility model [CM]) that allows for simple extraction of parameters for evaluation. Total power (amplitude) of the CM, the location of its apex, and the width/spread of the electrical activity are estimated 10 times a second (10 Hz).

Figure 7A:
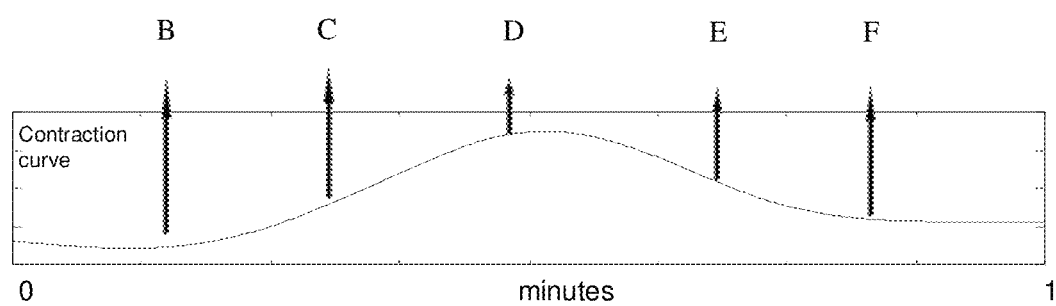
FIGS. 7A-7F compare a COMU against a two-dimensional contractility model (CM) of the electrical activity of the uterus and illustrate a contraction curve that graphs contraction activity over time.
Figure 7B:
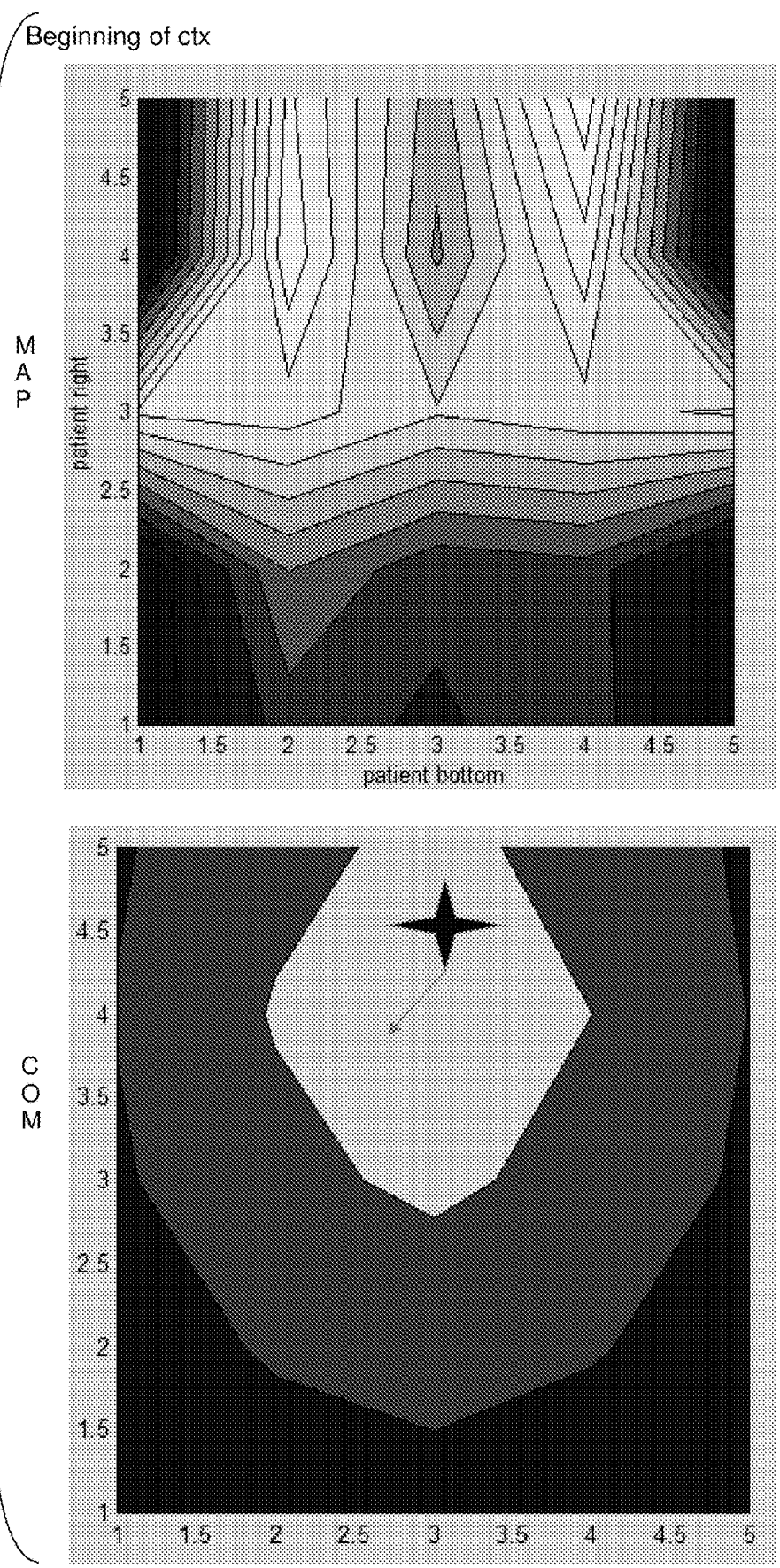
Figure 7C:
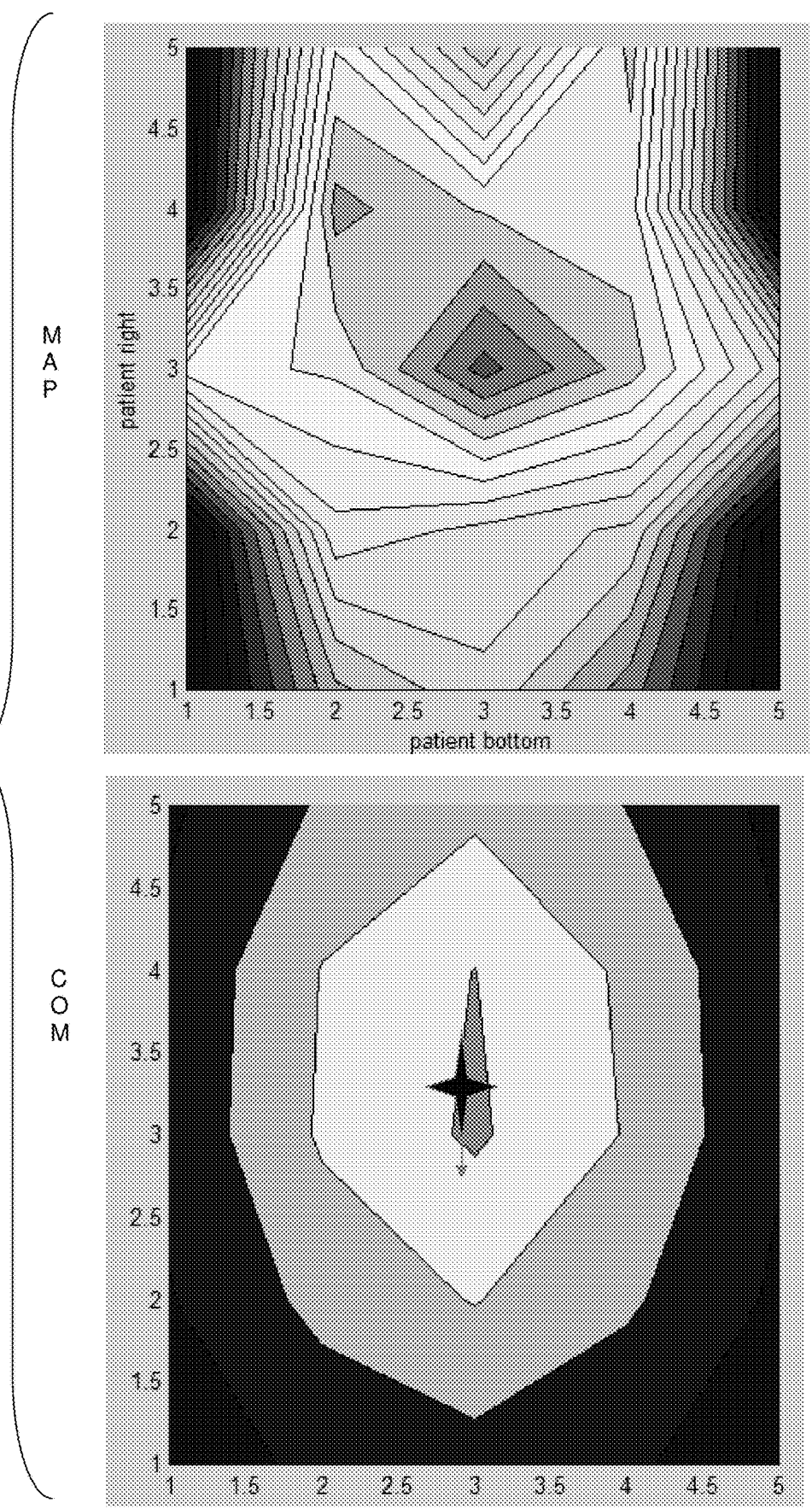
Figure 7D:
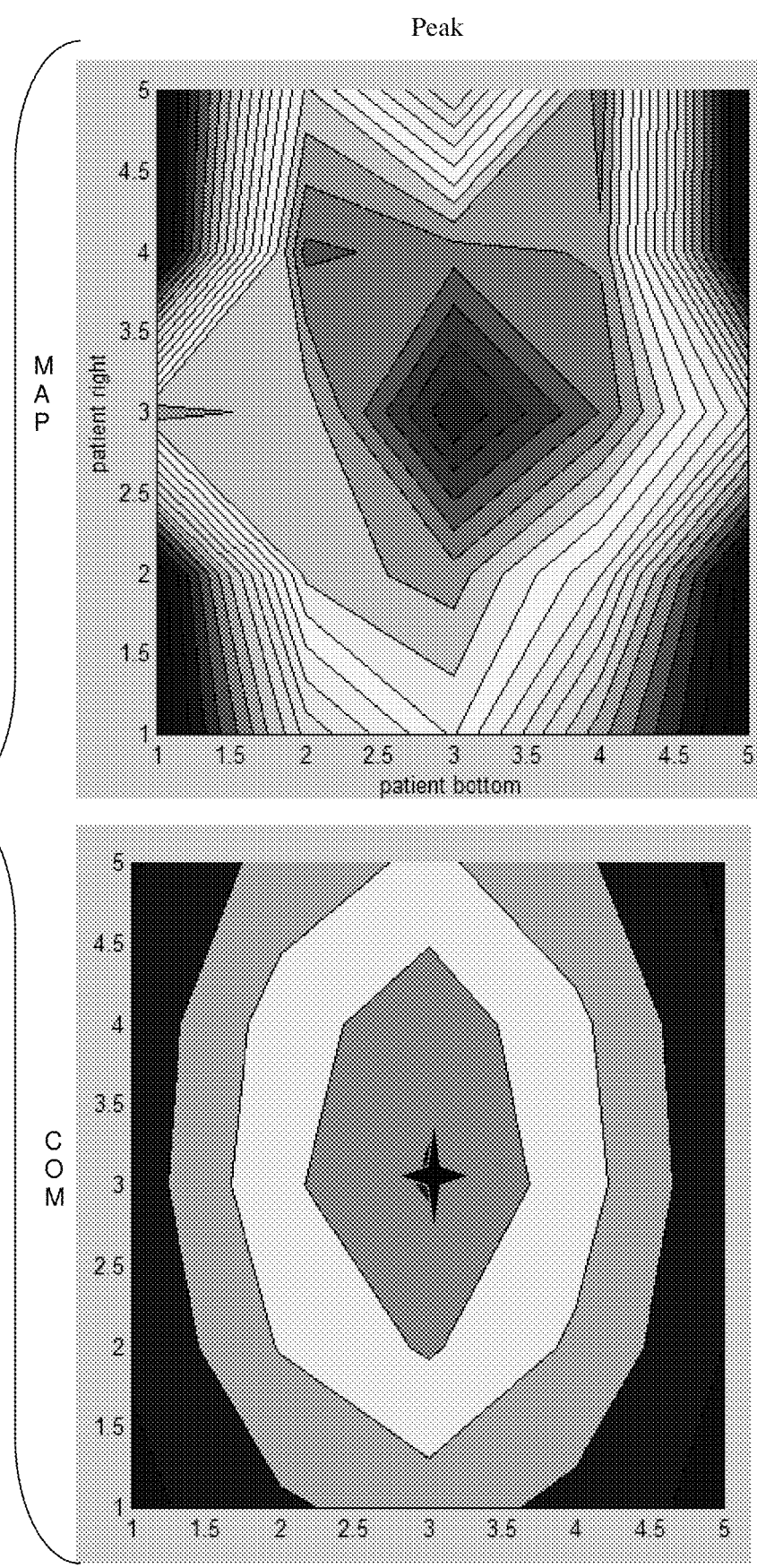
Figure 7E:
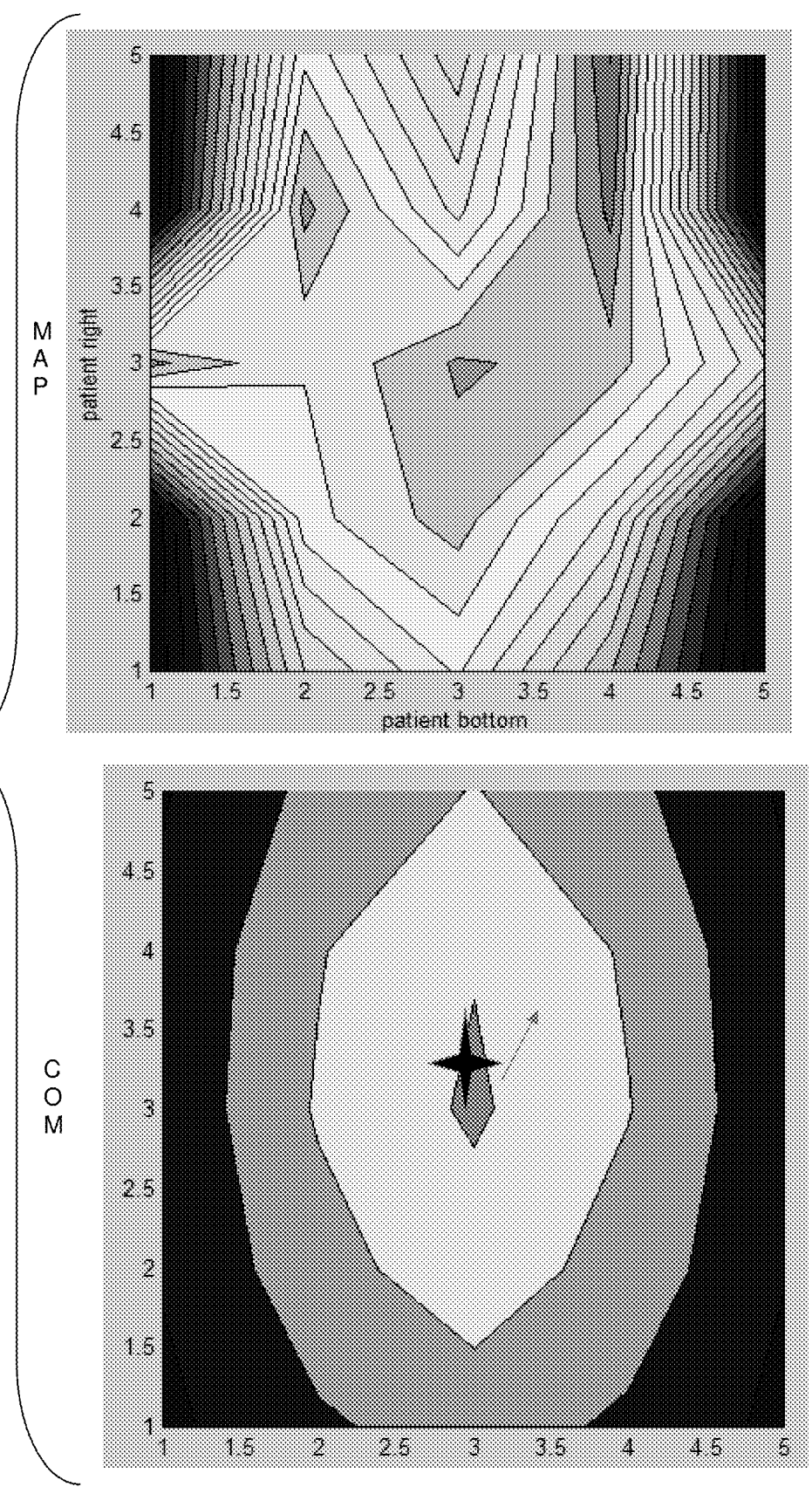
Figure 7F:
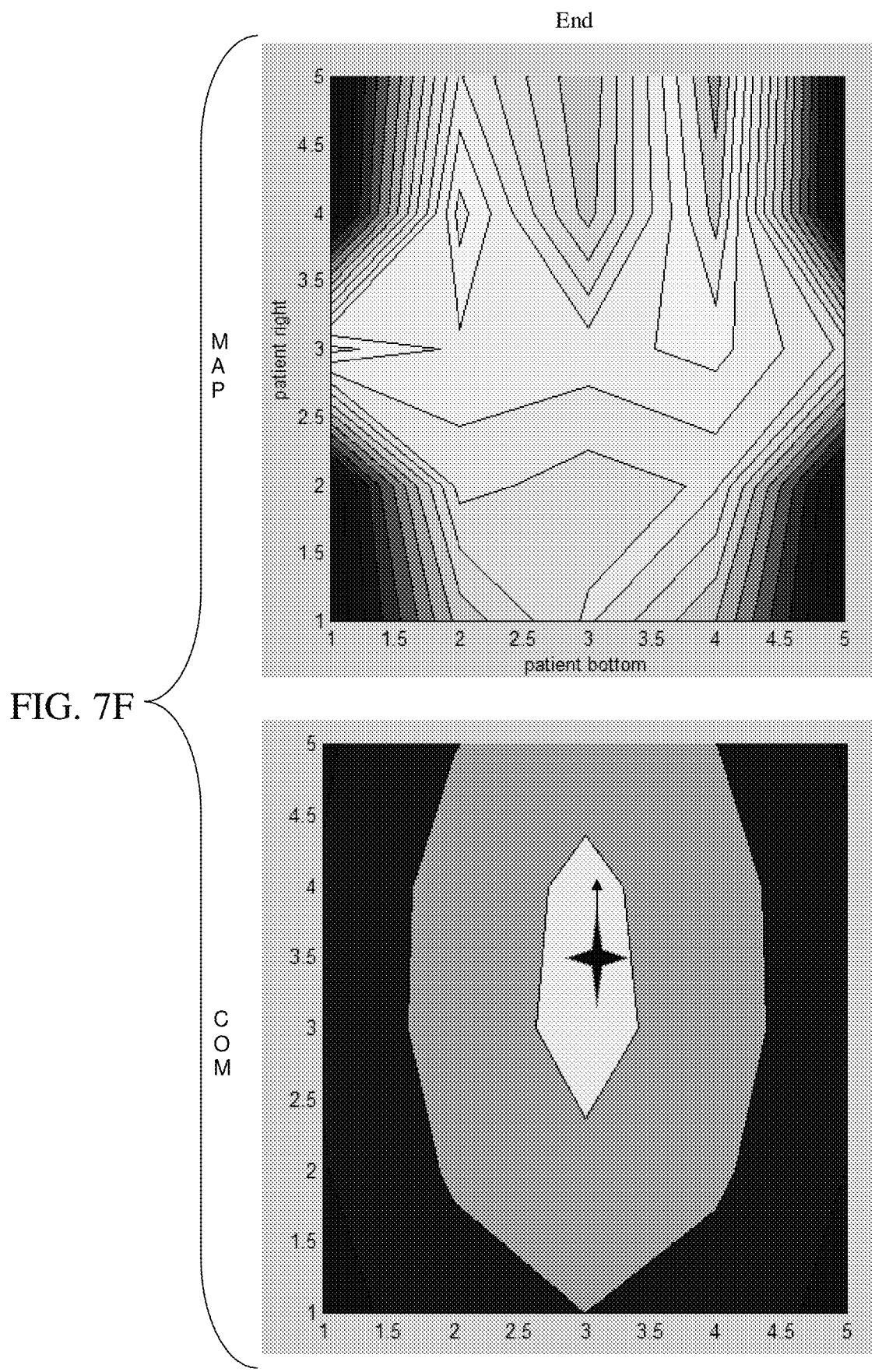

FIGS. 7A-7F illustrate an example of COMU and CM over time during a contraction. FIG. 7A is a graphical illustration of the progress of a contraction, where letters B-F on the graph correspond to the images shown in FIGS. 7B-7F. In FIGS. 7B-7F, the top image shows a COMU map displaying uterine activity, the image beneath is an image of the contractility model (CM) summarizing the uterine activity. FIG. 7B shows the COMU and CM before the contraction begins. FIGS. 7C-7F illustrate the progression of the contraction from left to right as shown at the bottom of FIG. 7A. Each successive image in FIGS. 7C-7F shows the spatial intensities of the contraction over the uterus and the motion of the apex of the contractility model during one contraction. For example, FIG. 7D illustrates peak contraction and FIG. 7F illustrates end of contraction.

From FIGS. 7A-7F, it is readily apparent that the illustrated contraction begins near the fundus, its apex moves down towards the cervix but stays midline, increases in strength, and subsides following the reverse pattern. In FIGS. 7B-7F, the spatial gradient of the CM is displayed by an arrow.

4. Average Contraction Over Time Operations

A useful parameter derived from the COMU is the average amplitude of the EHG envelope plotted over time, the COMU amplitude. Among other things, the COMU amplitude can create a signal similar to the IUPC. The COMU amplitude can be calculated using the following equation $$COMamp(t) = \sum_{i=1}^{5} \sum_{i=1}^{5} Z_{i,j}(t)/25$$

The beginning and end of contraction are defined using a threshold on the COMUamp. In one embodiment, the threshold is created by low pass filtering the amplitude curve at a very low frequency to detect the baseline of the curve. Preferentially, the filter is a 4$^{th}$ order Butterworth filter of cutoff frequency equal to 0.002 Hz. In another embodiment, the beginning and end of the contraction are detected by comparing consecutive moving average windows of different sizes. In one embodiment of the invention, to simplify the quantification of contraction parameters, the contraction is divided in two halves: from the beginning to the peak (T1), and the overall duration (T1+T2). The parameters extracted from the COMU are then compared during T1 and T2.

5. Spatial Location of the Contractile Peak and Variance Operations

The spatial location of the contractile peak is also a feature of interest. It is possible to also estimate the X,Y coordinate of the peak of the COMamp(t) by the following equations:

$$COMxaxis(t) = \sum_{i=1}^{5} i * Z_{i,j}(t)/COMamp(t)$$

$$COMyaxis(t) = \sum_{j=1}^{5} j * Z_{i,j}(t)/COMamp(t)$$

The equations can be calculated 10 times a second and detect the location of the peak of the contraction over the abdomen. Plotting the path of this maximum over time allows for the detection of contraction movements, both in the fundus/cervix and left-right directions. An example of this information is presented in FIG. 8. Substracting the values of the COMxaxis(t) and COMyaxis(t) found at the end and the beginning of a contraction (or half a contraction) gives the total (or half propagation) distance in the X and Y axis during a contraction. Dividing this values by the time taken to propagate gives us the speed of propagation during the entire (or half) contraction.

Figure 8:
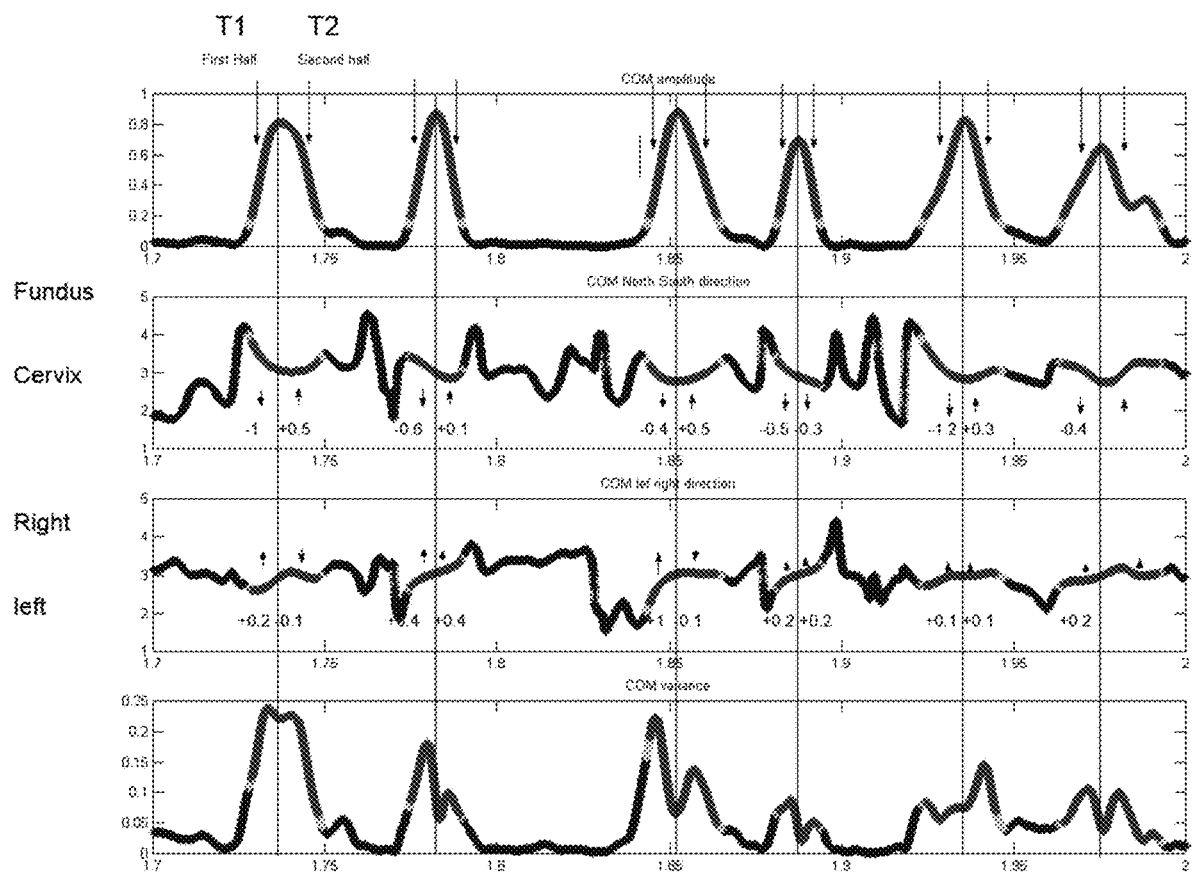
FIG. 8 illustrates CM spatio-temporal parameterization derived from the methods of the subject invention.

The first panel in FIG. 8 shows the mean overall amplitude over time, displaying 6 contractions. The red portions are the contractions, obtained with a threshold on the signal represented by the green segment. The first panel in FIG. 8 shows an example of the curve obtained with COMamp(t) which bears a strong resemblance to the IUPC, and is therefore indicative of the uterine pressure. The second and third panels show the movement of the apex of the contraction in the X and Y directions. The second panel shows the movement of the center of the contraction as defined herein, and in all these cases, the fundus to cervix movement during the ascending part of the contraction (T1) and the retraction during the descending part of the contraction (T2) are illustrated. The bottom-most, third panel shows the spread of the uterine electrical activity calculated as follows:

$$COM\ \mathrm{var}(t) = \sum_{j=1}^{5} (Z_{i,j}(t) - COMamp(t))^{\wedge}2$$

Using the panels of FIG. 8, it can be verified that for this patient the contraction occurs rather symmetrically since there is little right to left movement. Finally the first panel shows the evolution in time of the power of contraction. It is important to verify that the pressure seems to be higher during T1. The subject illustrated in FIG. 8 was one who underwent normal delivery; accordingly, the patterns illustrated in FIG. 8 are illustrative of normal patterns with corroboration from the literature.

6. Other Possible Modeling of the Contractile Map Operations

Operations to model the contractile map of the invention can be performed on a computing means (such as a computer processor), preferably in real time. In one embodiment, the contractile map modeling operations are performed by fitting a 2D Gaussian function to the map/image, which will automatically capture the amplitude, the location and the variances of the CM. The fitting can be done using any supervised learning algorithm (simple backpropagation, momentum, and the like). In one embodiment, the fitting is done using a Levenberg Marquadt and is checked by the residual of the fitting, yielding the following equation:

$$\text{Gauss}(t) = \text{GaussAmp}(t) * \sum_{i=1}^{5}\sum_{j=1}^{5} \exp\left(\frac{-((Z_{i,j}(t) - \text{meanGaussX})^{\wedge}2)}{\text{varGaussX}}\right) -$$

$$\frac{((Z_{i,j}(t) - \text{meanGaussY})^{\wedge}2)}{\text{varGaussY}}\Bigg)$$

The derivative in space of the model represents the Laplacian of the contraction, which is associated with the direction of propagation of the force generated by the contraction, i.e. Fundus-Cervix and Left-Right. There is evidence in the literature that efficient contractions push down the fetus, while non-productive contractions either form a standing wave or move upwards. Unlike the IUPC (being a scalar signal), which is unable to convey any information about spatial direction, the information derived in accordance with the subject invention can be used to estimate spatial gradients.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Preliminary Labor Dystocia Case-Control Study

Using spatio-temporal information collected with multi-channel EHG as described herein, patients that require cesarean delivery for labor arrest were identified from those who have a normal labor and vaginal delivery.

A cohort of patients who required cesarean delivery for active-phase labor arrest was extracted from a clinical database. These patients' records were each carefully reviewed for accuracy of surgical indication (based on the traditional definition of arrest: 2 hours of adequate uterine activity without cervical change) and then matched with two vaginally delivered controls with the following characteristics: a normal labor curve; EHG data available from the same cervical dilation as the arrest; and matching parity, gestational age, BMI, and induction. In the resultant 10 labor arrests and 20 controls, the spatio-temporal characteristics of contractions were analyzed at the same dilation and significant differences in the COMU were found. The movement of the CM apex over the course of contractions was mapped and then analyzed, with the resulting patterns over 30-minute windows positioned near the labor arrest.

In 16/20 (80%) of SVD controls, the predominant pattern during the second half of the contraction was an upward movement of the CM (that is, the contraction power was greater in the fundus than near the lower uterine segment [LUS]). The same was true for only 3/10 (30%) of those who underwent cesarean delivery for dystocia, p<0.01. Without being bound to any particular theory, it is hypothesized that this CM apex movement is a quantitative parameter of "fundal dominance" Recognizing that the definition of permanent arrest of dilation requiring cesarean delivery is a matter of debate, and that, with additional time, many of the cesarean patients would have eventually delivered vaginally, it is intriguing to speculate that CM outliers might actually be the group that were merely on a protracted labor curve.

Research Design and Methods

There are important features in the electrical activity of the uterus that differentiate functional and dysfunctional labor. Two distinct, but not mutually exclusive possibilities are considered herein: (1) there are features that predict short-term labor progress and (2) there are features (such as fundal dominance) that predict eventual labor outcome. While clinically known that oxytocin will often help labor progress by increasing the frequency of contractions, and often their power, it may be that oxytocin merely speeds an already 'functional' labor, while doing little for a truly dysfunctional labor (i.e. lacking fundal dominance). According to the subject invention, the electrical features of effective uterine contractions are identified.

The features indicative of short-term progress are investigated by studying patients who require labor augmentation. By dividing the patients into 'responders' and 'non-responders,' features that predict responsiveness to oxytocin and that provide a "short-term view" of labor progress can be delineated. Next, the long-term extremes—patients with normal labor progression and those with labor arrest that led to cesarean delivery—are examined to determine which features correlate with each labor outcome. Such information is useful in determining whether the short-term predictive features are also predictive of the long-term labor outcome of the patient. These analyses can provide key features that differentiate normal labor from arrested labor, short-term arrest from short-term dilation and also features that differentiate oxytocin response.

According to the subject invention, a large sample of labor segments can be used to train a multi-parameter model, the contraction efficiency indicator (CEI), to predict whether a subject is dilating normally. Similarly, using the same labor segments and knowledge of the eventual outcome, a multi-parameter model can be devised to predict labor outcome, the dystocia prediction indicator (DPI). These generated models provide important information regarding spatio-temporal EHG data that can be used to predict short-term labor progress and/or eventual labor outcome.

Example 2—Creation of Contraction Efficiency and Dystocia Prediction Indicators Based on the EHG Spatio-Temporal Contraction Patterns and Extracted Parameters Clinical Data Two sources of clinical data can be utilized. Over the past five years, 493 datasets from actively laboring women have been accumulated using the amplifier and data collection system described previously. This data set includes 388 term patients, 61 of whom underwent cesarean delivery. Information stored in the database includes: maternal age, height, weight, race, any diagnoses, obstetric history, labor onset (spontaneous versus induced), membrane status (artificial versus spontaneous rupture, time), gestational age, fetal presentation, estimated fetal weight, all cervical examinations (including dilation, effacement and station), all medications administered with dose and time, continuous cardiotocographic and all data from the abdominally sited electrodes including individual impedances, and information regarding the type of delivery, newborn weight and Apgar scores. Patient subsets from this database are suitable for initial design of the predictive models:

Dystocia case-control cohort: as described above, 10 patients who required cesarean delivery for active-phase labor arrest were each matched with two vaginally delivered controls with a normal labor curve, who were monitored at the same dilation as the arrest patients. Subjects were matched for parity, gestational age, BMI, and induction vs spontaneous labor.

Dystocia cohort: 30+ patients who underwent eventual cesarean delivery for "failure to progress" will be reviewed for accuracy of recorded surgical indication.

Oxytocin augmentation cohort: Approximately 80% of the database subjects received oxytocin augmentation. A cohort of 100 term patients in spontaneous labor who underwent oxytocin augmentation during the active phase and subsequently delivered vaginally are extracted. Chart review will be used to confirm spontaneous onset of labor, indication for oxytocin augmentation (dilation <1 cm/hr), cervical exam at least every 3 hours after oxytocin initiation, and lack of complicating factors such as chorioamnionitis and macrosomia.

Prospective arrest cohort: A prospective study will be performed throughout the study period using the same data collection protocol described in Preliminary Studies: term (≥37 weeks gestation) patients in spontaneous labor with a single viable fetus in cephalic presentation at ≥5 cm (active phase) who are diagnosed with arrest (no cervical change in two hours) and have no bleeding or uterine scar will be eligible for inclusion. After informed consent and initiation of EHG monitoring, an IUPC will be placed and oxytocin augmentation begun according to the standard labor unit protocol (increases at 30-minute intervals until MVUs are 150-250 or there is cervical change). Cervical exams will be performed and recorded every two hours. Additional data to be collected includes maternal demographic data, labor information (details of onset, membrane rupture, cervical exams, oxytocin dosages, and interventions), delivery newborn information (mode of delivery, newborn weight and Apgar scores), and the continuous output of the cardiotocograph monitor. These will be stored with the EHG data for subsequent analysis.

EHG Analysis

The amount of information contained in the COMU representation of uterine activity is very large. One approach for facilitating and obtaining systematic feature/parameter extraction is to first model the COMU with a signal processing methodology and then parameterize the model. As described above, the contractility model (CM) consists of a simple weighted average of the image. The peak, motion of the peak, and spread of the activity are then identified.

CM fit criteria. Before comparing models, criteria must be defined for evaluation. The criteria used in this Example is the power of the residuals [R(t)] coregistered in space i.e., measured between the estimated values of contractility and the measured ones at the electrodes.

$$R(t) = \frac{\sum_{frame\_t}(y_{comu}(i) - y_{com}(i))^2}{25}$$

The power of the residuals determines how closely the CM model fits the activity map.

The weighted average CM is very easy to compute. In other embodiments, spatial models such as the Mixture of Gaussians model can be fit to the EHG channels to provide CM fit criteria. The power of the residual fit can be used as the criterion to find a reasonable model order. Circular symmetric and asymmetric models can also be evaluated.

Quantification of the Movement of the Apex Over the Uterus.

One of the key attributes for determining uterine activity effectiveness is the spatial relationship of the uterine electrical activity and its movement over time (e.g. fundal dominance). Automatically quantifying this movement is possible once the CM is obtained. Several parameters can be derived from the quantification of the movement of the CM apex. Based upon previous work (Seitchik J, Chatkoff M L: Intrauterine Pressure Wave Form Characteristics of Successful and Failed 1St Stage Labor. Gynecologic Investigation 1977; 8: 246-53; and Althaus J E et al., Cephalopelvic disproportion is associated with an altered uterine contraction shape in the active phase of labor. Am J Obstet Gynecol 2006; 195: 739-42) indicating that uterine activity differences between the rising and falling portion of the contraction are significant, the contraction is divided into ascending and descending portions. The motion in each portion is then quantified using the following steps:

Determine the beginning and end of the contraction using a dynamic threshold on the CM amplitude.

Identify the spatial location of contraction onset.

Divide the contraction into its ascending part (from the beginning to the peak, T1) and descending part (from the peak to the end of the contraction, T2). The overall contraction duration is therefore T1+T2.

Quantify the change in the location of the apex in the Y (fundus-cervix) axis during T1 and T2. For simplicity, it can be assumed that the apex of the CM either moves upward or downward, leaving four possibilities for each contraction:

"Down and Up". The CM starts at the fundus, moves down on the abdomen then back up to the fundus.

"Down and Down". The CM moves downward throughout the contraction.

"Up and Up". The CM starts low then moves upward until the end of the contraction.

"Up and Down". The CM starts low, moves upward then back down toward the cervix.

In the subject invention, those contractions with higher fundal power at the end of the contraction ('Up' during T2) are defined as fundal dominant, and those whose initial onset is at the fundus are defined as having fundal origin.

Parameters for Evaluation.

In addition to the general motion of the electrical activity on the abdomen, a number of other parameters can be derived from the CM, specifically deriving parameters that correspond to known physiologic phenomena. From a clinical perspective, it is believed that effective contractions: (1) occur with a frequency of at least 3 per 10 minutes (2) have a pressure above 24 mmHg; (3) have strong fundal dominance; (4) are synchronous across the uterus; (5) are regular in rhythm, intensity and form of contraction; and (6) have relaxation periods between contractions.[37] Biomedical signals are notoriously contaminated with artifacts and noise. With this in mind, multiple parameterizations of each of these phenomena can be assessed to determine which formulation is most robust to noise. The initial parameterization will be as follows:

Fundal Dominance: Percentage of contractions that exhibit upward movement of the CM apex during T2, duration of time there is a fundal to LUS gradient of uterine activity, and the ratio of the total uterine activity in each segment.

Fundal Origin: Percentage of contractions that originate in the fundal region and the average Y-axis apex starting position.

Propagation time (Synchrony): the time from earliest onset of the contraction, to onset of contraction in the most delayed portion of the uterine map. Propagation distance will also be calculated and analyzed.

Regularity: the variance of the period between contractions and more complex regularity measures such as approximate entropy. See Althaus J E et al., Am J Obstet Gynecol 2006; 195: 739-42.

Quiescence (EHG activity between contractions): total EHG signal power will be quantified and graded from 0 (minimal activity) to 2 (significant activity), with definitions determined experimentally.

Example 3—Multi-Parameter Model that Predicts Labor Progress Resulting in a Contraction Efficiency Indicator The parameters derived in accordance with the subject invention can be applied to oxytocin-augmented labors to investigate their predictive value. In one embodiment, a contraction efficiency indicator can be created using a dilation score for each contraction, like the ultrasound system described by Sharf et al. (Continuous monitoring of cervical dilatation and fetal head station during labor. Medical Engineering & Physics In Press, Corrected Proof). In another embodiment, the efficiency of a group of contractions is estimated between measurements of dilation.

Patients from the Oxytocin Augmentation Cohort described above can be used for this analysis. Labor curves are plotted for determination of slope prior to augmentation, at the next cervical examination and after maximum oxytocin dose was reached. Thus, there are four groups for analysis (FIG. 9).

Figure 9:
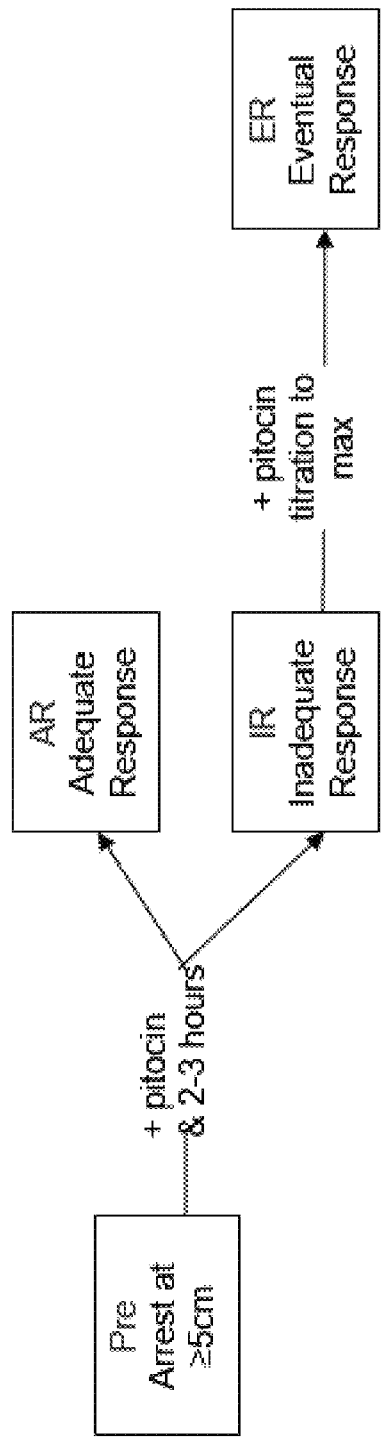
FIG. 9 is a flow diagram illustrating the steps involved in oxytocin augmentation.

As illustrated in FIG. 9, 'Pre' is the 30-minute segment during arrest, prior to the initiation of oxytocin. Response ('AR' and 'IR') is the 30-minute segment around the next cervical exam, 90-180 minutes following initiation of oxytocin. For those with an initially inadequate response, Eventual Response (ER) is the 30-minute segment around the cervical exam at the maximal oxytocin dose. Adequate response (AR) and Eventual Response (ER) are defined as resumption of dilation (>1 cm/hr). Inadequate Response (IR) is slower or lack of dilation.

Comparisons of interest include:

Pre versus AR: identify parameters that indicate a positive response to oxytocin that leads to cervical dilation.

Pre versus IR: identify parameters that indicate a negative response to oxytocin, one that does not lead to cervical dilation.

AR versus IR: distinguish between progressing and non-progressing augmented labor.

IR versus ER: recognize when the augmented labor does begin to progress.

Prediction values for each comparison can be analyzed by univariate analysis using Mann-Whitney U-test for assessment of continuous variables (e.g. fundal dominance, fundal origin, propagation time), and Fisher's Exact Test for categorical variables (e.g. quiescence). Parameters with a significant correlation are applied in a logistic regression model to determine independent predictors of oxytocin response. Parameters with P>0.2 are dropped.

The parameters that are uncorrelated with other retained parameters are preferentially retained to provide a list of parameters that independently correlate with cervical dilation in response to augmentation, short-term markers of contraction efficiency.

Simple models can be created based on the knowledge gained and the parameters derived above. The models produce a dichotomous output indicating whether the cervical dilation at the next exam interval will be adequate (>1 cm/hr) or inadequate (<1 cm/hr). The models are logistic regression and/or neural networks. In effect, a group of contractions can be labeled as efficient or not efficient at creating short-term changes in dilation. Temporal averaging of the contraction parameters can then be utilized for use in evaluating optimal window sizes experimentally.

From the entire database of term laboring women, segments from active labor that are bounded by cervical examinations and are 90-180 minutes in length can be extracted to train a computing means (i.e., intelligence means such as an artificial neural network). Preferably, several hundred segments of EHG are used for analysis with a known outcome: cervical change over the interval. The contraction efficiency indicator (CEI) can be trained on 75% of the segments, and tested on the remaining 25%. The results can be evaluated with positive and negative predictive values and ROC analysis.

Example 4—Multi-Parameter Model that Predicts Labor Outcome Resulting in a Dystocia Prediction Indicator According to the subject invention, parameters that differentiate the uterine activity patterns of patients with normal labor (successful vaginal delivery) versus those with dysfunctional/arrested labor are determined. The Dystocia case-control cohort described above can be implemented. Additional cases identified in the Prospective arrest study (described above) and matched with controls can be added to this cohort. Specifically, the 30-minute period at diagnosis of arrested labor compared with 30-minutes at the same dilation in the matched controls will be determined.

Each of the EHG Parameters for Evaluation will be calculated on the 30-minute segments and compared between the two extremes of normal labor and cesarean for dystocia. Prediction values of labor failure can be analyzed by univariate analysis as described above. Parameters with significant correlation or tendency with outcome (p<0.25) are retained. Since these parameters are used to build a continuous dystocia prediction indicator, parameters that are uncorrelated with other significant parameters are preferentially retained. The ability of the adequate dilation parameters (short-term contraction effectiveness) to predict the long-term success of the patient to deliver vaginally is of particular interest. This result can assist in elucidating the fundamental questions of how the uterine electrical activity patterns influence short and long-term labor effectiveness.

Linear regression and/or neural network models can be developed to predict the eventual outcome of labor (vaginal delivery or cesarean for dystocia, ignoring cesareans for other indications). A model is created that will accept the EHG pattern of electrical activity from a set of contractions and label them; a group of contractions can be labeled functional or not functional relative to the capability of the contractility pattern to produce vaginal delivery. In one embodiment, temporal averaging of the features over each time window will be utilized. The time window to group the contractions and the relationship between the patterns at various levels of cervical dilation can be experimentally determined.

For the DPI model building, both the Dystocia cohort (all monitored patients who delivered by cesarean for failure to progress, regardless of whether they were monitored at the time of arrest) and all patients who delivered vaginally can be utilized. From these subjects, each 2-hour segment from 5 cm dilation to the onset of pushing or end of collection is extracted, together with dilation at the start of the segment (estimated by assuming linear dilation between the most recent and first subsequent cervical examinations), and eventual labor outcome. This provides several hundred segments of EHG for analysis with a known outcome, though a disproportionate number will be successful augmented vaginal deliveries. The samples can be divided so that equal percentages of segments from dystocia and successful delivery patients are in the testing and training sets. Both linear and non-linear (neural network, in particular multi-layer perceptron) models can be evaluated for this task and compared using positive and negative predictive values and ROC curves with AUC analysis.

Example 5—Clinically Evaluate and Refine the Contraction Efficiency and Dystocia Prediction Indicators Prospective Evaluation of the Contraction Efficiency Indicator (CEI)

Continuing the Prospective Arrest study described above, FIG. 10 describes the eventual outcomes. Patients enrolled during this phase undergo the same monitoring as described above, however the data collection computing means also displays the CEI, as derived by the predictive models. Cervical exams continue at two-hour intervals, but an additional cervical check can be indicated in the following circumstances: (1) for the patient with initially inadequate MVUs, 30-minutes after the target range (150-250) is achieved; and (2) for the patient whose initial CEI identified inefficient contractions, 30-minutes after effective contractions are identified. Pitocin titration are based on traditional guidelines only (MVUs and/or presence of cervical change).

Each cervical examination is considered a data point. Each point includes the elapsed time since the last cervical examination, and three dichotomous values: presence of cervical dilation (Dil+ if change noted), CEI status (CEI+ if it predicts cervical change over the segment), and MVU status (MVU+ if 'adequate' at 150-250). It is estimated that an average of 3-4 data points can be generated for each patient, based on the 2-hour maximum interval between cervical examinations, the 'modern' average active phase dilation time of 5.5 h to 7.7 h for nulliparas and 5.7 h for multiparas (Zhang J et al., Reassessing the labor curve in nulliparous women. American Journal of Obstetrics and Gynecology 2002; 187: 824-8; and Albers L L et al., The length of active labor in normal pregnancies. Obstetrics and Gynecology 1996; 87: 355-9) and the fact that these patients are enrolled at arrest.

Figure 10:
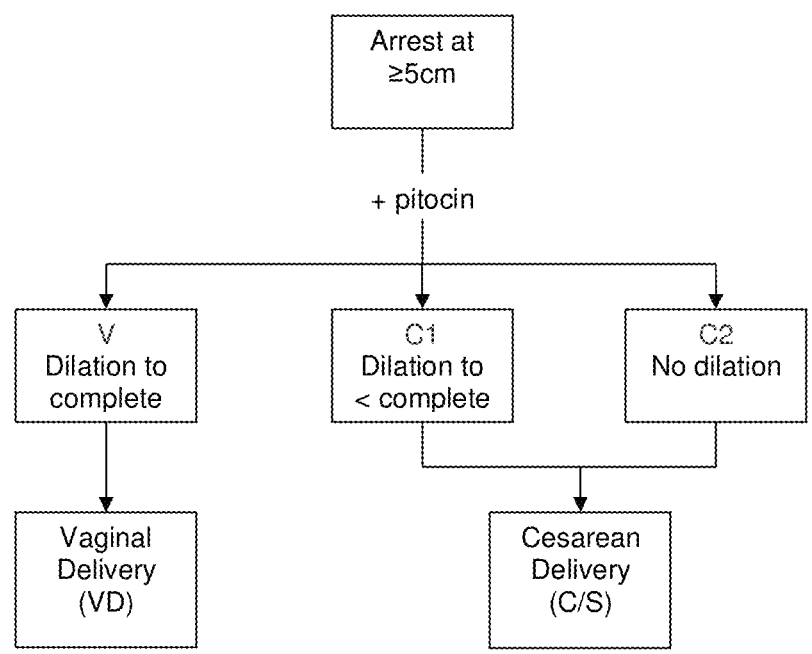
FIG. 10 is a flow diagram illustrating various outcomes resulting from arrested labor.

To determine the likely patient population in each outcome of FIG. 10, data can be extrapolated from the study of Rouse et al. (Active phase labor arrest: revisiting the 2-hour minimum. Obstetrics & Gynecology 2001; 98: 550-4) where they allowed patients to labor for an extended period of time. They found that 85% (nulliparas) to 94% (multiparas) of those with MVU+ will deliver vaginally (Del+). Similarly 83% (nulliparas) to 97% (multiparas) of those who never achieve adequate MVU (MVU−) will also delivery vaginally. This study also shows that MVUs are an inaccurate measure of dilation and successful delivery. Thus, the CEI has ample opportunity to improve upon the prediction capabilities of MVU for cervical dilation, even with a relatively small sample size.

The model's prediction of the presence or absence of cervical change at each exam can be compared with a prediction based on MVUs using Chi-square analysis. Desirable outcomes include (a) ability to identify 'adequate' uterine contractions as well as the IUPC (CEI+ when MVU+), obviating the need for this invasive device; (b) ability to identify effective uterine contractions better than the IUPC (CEI+ when MVU− yet cervical dilation ensues) and identifies the minimum effective oxytocin dose, perhaps lowering the total dose required, together with side effects; (c) ability to identify inefficient uterine contractions despite 'adequacy' by MVUs (CEI− when MVU+), speeding diagnosis of arrest.

Example 6—Evaluation of the Dystocia Prediction Indicator

Since the DPI evaluation does not affect the study protocol, both the prospective CEI cohort and the prospective arrest cohort described can be utilized for this study. An obstetrician (RKE) reviews all records to confirm diagnosis and surgical indication. Patients who undergo cesarean delivery for other indications are excluded (e.g., fetal heart rate tracing abnormalities or failure of descent after complete cervical dilation), which is an estimated 25% of the patients. DPI can be calculated over several intervals: since enrollment, over the interval since the last cervical examination, and over the last 30-minutes. Additional data at each point can include elapsed time since dystocia diagnosis and since last cervical examination, current cervical dilation, and eventual outcome.

Extrapolating from the work of Rouse et al. (Active phase labor arrest: revisiting the 2-hour minimum. Obstetrics & Gynecology 2001; 98: 550-4) 55% (nulliparas) to 73% (multiparas) will progress in labor in the first 2 hours of augmentation (Groups V+C1). The number of patients in each group depends on the attending obstetrician's comfort delaying delivery. The three DPI calculation intervals can be compared for positive and negative predictive values and separate ROC curves can be generated and compared via the area under the ROC curve. With this data, greater patient numbers and greater control over the management of the patient can be achieved with appropriate safety measures.

Example 7—Non-Invasive External IUPC Prediction

Optimal linear filtering was applied to EHG signals extracted in accordance with the subject invention. In 14 patients who were monitored with both EHG and IUPC, a Wiener filter was used to predict the IUP from the EHG recording (Skowronski M D et al., Prediction of intrauterine pressure from electrohysterography using optimal linear filtering. IEEE-TBME 2006; 53: 1983-9). MVUs were independently calculated by an obstetrician and two labor nurses who were blinded to both patient and EHG vs IUP output. The EHG-derived MVUs correlated with IUP ($r=0.795$; $p<0.0001$), but mathematically differed by $17\pm20\%$ with 83% of EHG MVUs underestimating the IUP. EHG detected 98% of 362 IUP contractions, with 8% over-detection. Contraction duration was similar ($56.4\pm11.9$ sec vs. $55.7\pm13.0$ sec, for IUP and EHG, respectively). It was concluded that EHG predicts contraction frequency and duration well, but application of the Wiener filter does not sufficiently correlate with IUP to be clinically useful. See Skowronski M D et al., IEEE-TBME 2006; 53: 1983-9.

Recognizing how well the EHG detects contractions, a population in which non-invasive uterine activity monitoring frequently fails was studied: the morbidly obese population (Euliano T et al., Prediction of Intrauterine Pressure Waveform from Transabdominal Electrohysterography. Journal of Maternal-Fetal & Neonatal Medicine. 2006). 26 patients with BMI ≥34 in whom an IUPC was placed during EHG monitoring were reviewed. Thirty-minute segments before and after IUPC placement were evaluated. For detection of contractions, EHG signals extracted in accordance with the subject invention correlated much more closely with the IUP tracing (0.94±0.06), than with the tocodynamometer (0.77±0.25), p=0.002. This confirms the value of simple uterine activity monitoring with the EHG signals extracted herein, and suggests its superiority to tocodynamometers.

Example 8—Spatio-Temporal Analysis of Uterine Contractions Related Vaginally Delivered Patients and Those Requiring Cesarean Delivery for Active-Phase Labor Arrest Materials and Methods Patients' skin were prepared by gentle rubbing with abrasive gel and 10 3-cm$^2$ Ag/AgCl$_2$ electrodes (Ambu; Glen Burnie, Md., USA) were positioned on the maternal abdomen (FIG. 1A). The electrodes were connected to an amplifier in a monopolar fashion with centrally located common reference and common mode rejection leads. Electrode positions were modified slightly for each patient, as required by the location of the tocodynamometer and ultrasound fetal heart rate monitor, but the midline fundal and suprapubic locations were fixed. Impedance of each electrode was measured (as compared with the reference) (General Devices EIM-105 Prep-Check; Ridgefield, N.J., USA). Skin preparation was repeated as needed at each site until the measured impedance was below 10 kΩ where possible. The 8 recorded signals were fed to an 8-channel high resolution, low-noise unipolar amplifier specifically designed for fetal ECG signals. All 8 signals were measured with respect to the reference electrode. The amplifier 3 dB bandwidth was 0.1 to 100 Hz, with a 60-Hz notch filter. The amplifier had a variable gain, but for our purposes the gain was set to 6,500. The data were transferred to a personal computer via a 16-bit resolution A/D card and stored at a 200-Hz sampling frequency. In addition to electrical signals, data from the standard maternal-fetal monitor (Corometrics, GE Medical Systems) were also collected for comparison. The EHG-derived contraction curve was viewed by the research personnel and was not used for patient care.

Patients who underwent primary cesarean delivery for labor arrest after achieving at least 5-cm cervical dilation and had EHG monitoring with the final amplifier design (two-versions) for at least 30-minutes during the period of arrest were analyzed. Patients were excluded if they had a uterine scar due to the increased rate of repeat cesarean delivery in this population (Landon M B et al., Maternal and perinatal outcomes associated with a trial of labor after prior cesarean delivery. N Engl J Med 2004; 351: 2581-2589). Each potential subject's chart was reviewed by a maternal-fetal medicine specialist (RKE) to confirm the diagnosis (arrest of dilation at cm, and no other indication for cesarean delivery). Each of these index subjects was matched with two vaginally delivered controls with no prior cesarean delivery and a normal labor curve (active phase dilation >1 cm/h). The subjects were matched for gestational age ±2 weeks, BMI ±10, parity (nulliparous or parous), induction versus spontaneous labor, and EHG monitoring during dilation within ±1 cm of the dystocia. These matching criteria were selected by RKE based on factors likely to affect labor outcome. Parity, maternal size, and induction status are supported by Hin et al. (Antepartum and intrapartum prediction of cesarean need: Risk scoring in singleton pregnancies. Obstet Gynecol 1997; 90:183-186).

Sixteen cesarean delivery patients met the inclusion criteria; two were excluded for unusable data (amplifier saturation during collection and low signal-to-noise ratio), and two for lack of matching controls. The remaining 12 index subjects were successfully matched with the nearest two vaginally delivered controls that met the criteria above. Upon reviewing the EHG data for the controls, some had noise in the signal at the dilation of interest (determined by assuming a linear dilation rate between surrounding cervical examinations), thus the dilation at the segment used occasionally varied by more than ±1 cm of the dystocia, but never more than ±2 cm.

EHG Analysis

Figure 14:
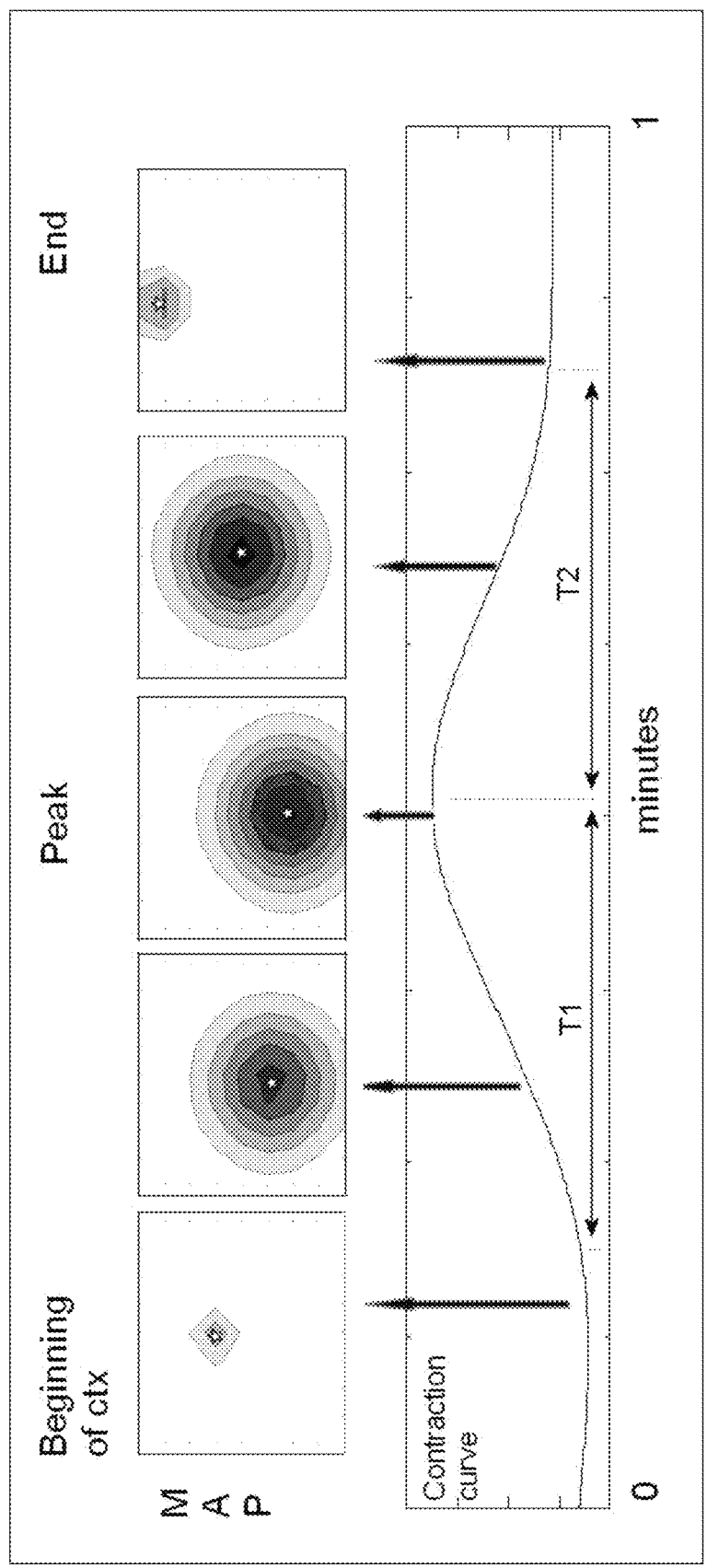
FIG. 14 illustrates another simplified representation of uterine activity, where the center of uterine activity is denoted by the star in each figure and its vertical motion over time can be tracked.

From the 8 individual electrode signals (FIG. 3), pair-wise subtraction between neighbors removed common signal characteristics and provided local information about the uterine electrical activity pattern. After channel normalization, rectification and filtering (Butterworth low pass filter with a cutoff at 0.02 Hz), these signals represented the local contraction strength at 17 locations over the abdomen, displayed as a 5×5 grid (FIG. 5). This grid was calculated 10 times per second and the data interpolated over the abdomen and over time generating a real-time movie of the relative intensity of the uterine muscle activity over the abdomen (FIG. 6). From this uterine contraction map, a Gaussian model was used to determine the Center of Uterine Activity (CUA). FIG. 14 demonstrates the evolution of the electrical map during a sample contraction, with the intrauterine pressure shown in the curve at the bottom and the white star indicating the CUA. The vertical motion of the CUA was determined by its location at the beginning, peak and end of the contraction.

Using a 30-minute window positioned during the labor arrest, or near the same dilation in the controls, the vertical direction of CUA movement during each half of each contraction was calculated: T1=onset to peak, T2=peak back to baseline. The precise anatomic location of the Center of Uterine Activity was patient-dependent, varying with the exact location of the electrodes, therefore only the direction of the Center of Uterine Activity was analyzed.

When the contraction begins (FIG. 14, left), energy builds and spreads throughout the uterus. By the peak of the contraction (end of T1; FIG. 14, center), the vast majority of the uterus is contracting. Therefore, the direction of the Center of Uterine Activity during T1 depends primarily on where the contraction began. During T2 the contraction begins to subside. If the lower portion of the uterus begins to relax earlier than the upper portion, the Center of Uterine Activity moves upward (FIG. 14, right).

Finally, contraction patterns were classified as moving downward (toward the lower uterine segment (LUS)) or upward (toward the fundus) for each half of each contraction, resulting in four contraction patterns: "LUS-Fundal", "LUS-LUS", "Fundal-LUS", and "Fundal-Fundal". The percentage of each pattern in a 30-minute segment of data from each patient was calculated.

Statistics

Regression diagnostics, focused on residual analysis, led to the conclusion that the assumption of Gaussian errors was appropriate. For each arrest patient, the prevalence of each of the four contraction patterns was evaluated by calculating the average prevalence for the vaginal deliveries in each of the matched clusters and subtracting the prevalence of the associated cesarean delivery. The continuous percentage of the four contraction patterns was used because categorizing that variable would lose power for hypothesis testing and reduce the precision of the estimated odds. This difference was then tested using a 2-tailed Student's T test. Canonical discriminant (multivariate) analysis was used to gain statistical power for the small sample size. This established the relative significance of each labor pattern for predicting the outcome of cesarean delivery for dystocia. Logistic regressions compared the prediction of outcome based solely on the pairing variables, versus with the addition of the contraction pattern information. This regression allowed adjustment for the pairing covariates and produced Receiver Operating Characteristic (ROC) curves. A Chi-square statistic was calculated to summarize this comparison. Data were analyzed using the SAS system for personal computers (SAS Institute, Cary, N.C.).

Results

The average duration of arrest in the cesarean delivery cohort was 6±3 hours. All arrest patients and seventeen out of twenty-four (17/24) vaginally delivered patients received oxytocin augmentation. All patients had a sustained contraction frequency of every 1-3 minutes, and of the eleven (11) cesarean patients who had IUPC monitoring, all achieved Montevideo units (MVU) >150 mmHg. The groups were not significantly different with regard to the pairing variables (gestational age, BMI, dilation at monitoring), or in newborn weight or maternal age (FIG. 15). No patient experienced any adverse events related to skin preparation or the study protocol in general.

Figure 16:
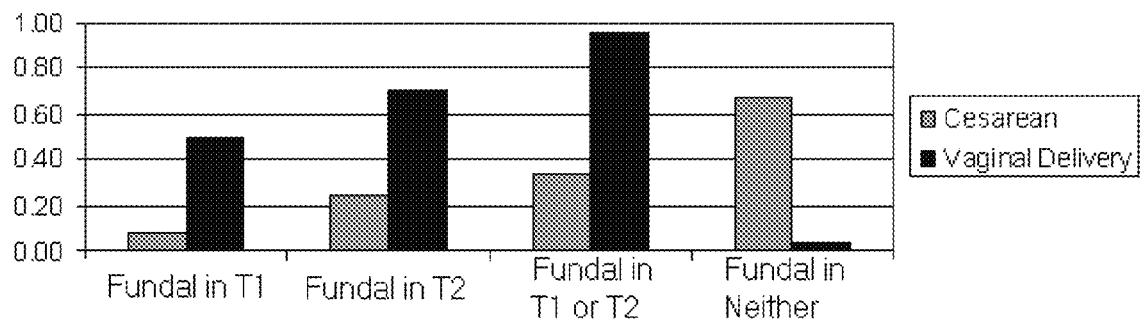
FIG. 16 graphically illustrates predominant patterns of center of uterine activity movement, where Fundal indicates movement of the CUA toward the fundus; T1 indicates the time from contraction onset peak; and T2 indicates the time from contraction peak to return to base.
Figure 17:
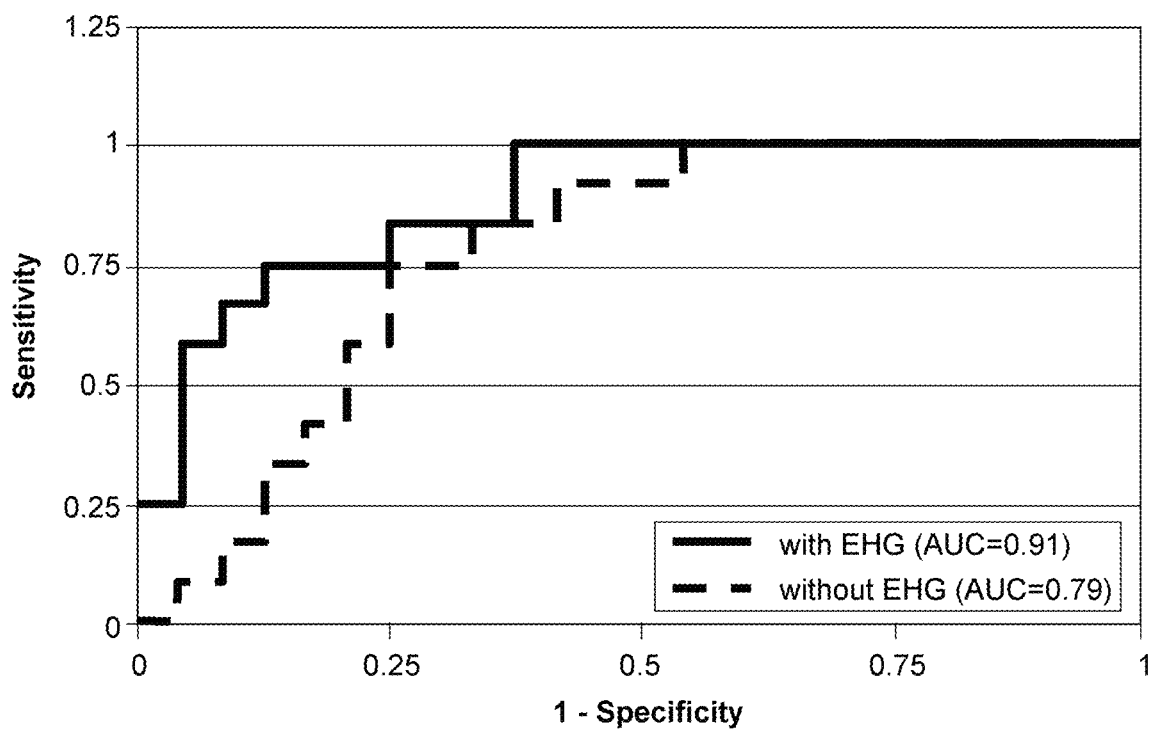
FIG. 17 graphically illustrates receiver operating characteristics curves for likelihood of labor arrest and cesarean delivery using matching criteria (gestational age, body mass index (BMI), spontaneous versus induced labor, and dilation time of study) with or without the addition of EHG data.

Predominantly fundal movement of the Center of Uterine Activity was more common in those dilating normally (FIG. 16). During T1, twelve out of twenty-four (12/24) vaginally delivered patients versus one out of twelve (1/12) cesarean delivery patients had a predominantly fundal CUA direction. Similarly, during T2 seventeen out of twenty-four (17/24) vaginally delivered versus thirteen out of twelve (3/12) cesarean delivery patients had the same pattern. Overall, twenty-three out of twenty-four (23/24) vaginally delivered patients had a predominantly fundal CUA direction during T1 and/or T2, compared with four out of twelve (4/12) for the cesarean delivery cohort. Comparing each pattern, two differed significantly between the groups: LUS-LUS was more common in cesarean delivery patients (p=0.015), while Fundal-Fundal was more common with vaginal deliveries (p=0.003). Logistic regression analysis using only the pairing variables—gestational age, BMI, parity, spontaneous versus induced labor, and dilation at the time of study—to predict outcome (cesarean for arrest versus vaginal delivery), resulted in an area under the ROC curve (AUC) of 0.79. Upon adding 3 of the 4 dilation patterns (because the fourth would be ipsative), the AUC increased to 0.91 (FIG. 17). Calculating a Chi-Square value of 13.090 for the difference between two models' log likelihood score gives a p value=0.004, indicating the addition of the dilation patterns is a significant predictor of delivery type.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A uterine monitoring system, comprising:
 a plurality of surface sensors suitable for attaching to a patient's abdomen and receiving uterine electrical signals;
 a user interface;
 one or more processors;
 a connector interface that is connected to the plurality of surface sensors; and
 a non-transitory computer readable medium storing computer software that, when executed, causes the one or more processors of the uterine monitoring system to:
  receive or determine a location of each of the plurality of surface sensors and recording the location of each of the plurality of surface sensors;
  record electrical signals from each of the plurality of surface sensors over time;
  convert the electrical signals from each of the plurality of surface sensors into contraction intensity information;
  create a movie comprising a plurality of uterine contractile maps based on the location of each of the plurality of surface sensors;
  determine a center of uterine electrical activity based on the plurality of contractile maps;
  track movement of the center of uterine electrical activity to establish a contraction pattern, wherein the contraction pattern is based at least in part on a percentage of time the contraction pattern occurs within a period of time; and
  based on clinically relevant findings stemming from the contraction pattern, diagnose normal or abnormal labor.

2. The system of claim 1, wherein the computer software, when executed, further comprises a function for sequentially analyzing the plurality of uterine contractile maps to extract information about the contraction pattern.

3. The system of claim 2, wherein the computer software, when executed, further causes the one or more processors of the uterine monitoring system to:
 extract the information about the contraction pattern including time and location a contraction starts, extent of the contraction, a direction of contractile propagation, and a spread and a speed of contractile propagation over the patient's abdomen from the sequentially analyzed plurality of uterine contractile maps.

4. The system of claim 2, wherein the computer software, when executed, further causes the one or more processors of the uterine monitoring system to:
 perform an electrohysterogram (EHG) extraction function that analyzes the electrical signals to extract the following parameters from a grid of locations corresponding to the plurality of surface sensors: time of contraction, location of contraction, extent of contraction, direction of propagation, speed of propagation over the abdomen, average contraction amplitude of an EHG envelope over time, spatial location of the peak of contraction and variance, spread of the contraction, abdominal intensity distribution, abdominal frequency distribution, patterns of contraction intensity over time, distance of peak power propagation, power changes over time, and frequency changes over time from the sequentially analyzed plurality of uterine contractile maps; and use the parameters to quantify the contraction pattern to predict labor outcome.

5. The system of claim 1, wherein the computer software, when executed, further causes the one or more processors of the uterine monitoring system to:
generate location signals, from the electrical signals, by pair-wise subtraction between signal neighbors to remove common signal characteristics; and
provide local information about the contraction pattern.

6. The system of claim 1, wherein the computer software, when executed, further causes the one or more processors of the uterine monitoring system to apply a Gaussian model to estimate the center of uterine electrical activity based on the plurality of contractile maps.

7. The system of claim 1, wherein the computer software, when executed, further causes the one or more processors of the uterine monitoring system to fit a Gaussian function to the plurality of contractile maps to capture an amplitude, location, and variances of a contractility model.

8. The system of claim 6, wherein the Gaussian function is fitted to the plurality of contractile maps using a Levenberg-Marquardt learning algorithm.

9. A method for monitoring uterine contractility in a patient, comprising:
placing a plurality of surface sensors on a patient's abdomen and receiving uterine electrical signals;
receiving or determining, by one or more processors, a location of each of the plurality of surface sensors and recording the location of each of the plurality of surface sensors;
recording, by the one or more processors, electrical signals from each of the plurality of surface sensors over time;
converting, by the one or more processors, the electrical signals from each of the plurality of surface sensors into contraction intensity information;
creating, by the one or more processors, a movie comprising a plurality of uterine contractile maps based on the location of each of the plurality of surface sensors;
determining, by the one or more processors, a center of uterine electrical activity based on the plurality of contractile maps;
tracking, by the one or more processors, movement of the center of uterine electrical activity to establish a contraction pattern, wherein the contraction pattern is based at least in part on a percentage of time the contraction pattern occurs within a period of time; and
based on clinically relevant findings stemming from the contraction pattern, diagnosing normal or abnormal labor.

10. The method of claim 9, further comprising:
sequentially analyzing the plurality of uterine contractile maps to extract information about the contraction pattern.

11. The method of claim 10, further comprising:
extracting the information about the contraction pattern including time and location a contraction starts, extent of the contraction, a direction of contractile propagation, and a spread and a speed of contractile propagation over the patient's abdomen from the sequentially analyzed plurality of uterine contractile maps.

12. The method of claim 10, further comprising:
analyzing the electrical signals to extract the following parameters from a grid of locations corresponding to the plurality of surface sensors: time of contraction, location of contraction, extent of contraction, direction of propagation, speed of propagation over the abdomen, average contraction amplitude of an electrohysterogram (EHG) envelope over time, spatial location of the peak of contraction and variance, spread of the contraction, abdominal intensity distribution, abdominal frequency distribution, patterns of contraction intensity over time, distance of peak power propagation, power changes over time, and frequency changes over time from the sequentially analyzed plurality of uterine contractile maps; and
using the parameters to quantify the contraction pattern to predict labor outcome.

13. The method of claim 9, further comprising:
generating location signals, from the electrical signals, by pair-wise subtraction between signal neighbors to remove common signal characteristics and provide local information about the contraction pattern.

14. The method of claim 9, further comprising:
applying a Gaussian model to estimate the center of uterine electrical activity based on the plurality of contractile maps.

15. The method of claim 9, further comprising:
fitting a Gaussian function to the plurality of contractile maps to capture an amplitude, location, and variances of a contractility model.

16. The method of claim 15, wherein the Gaussian function is fitted to the plurality of contractile maps using a Levenberg-Marquardt learning algorithm.

17. A computer program product comprising one or more non-transitory computer-readable medium storing computer software that, when executed, causes a processor of a uterine monitoring system having a plurality of surface sensors to perform the steps of:
receiving or determining a location of each of the plurality of surface sensors disposed on a patient's abdomen and recording the location of each of the plurality of surface sensors;
recording electrical signals from each of the plurality of surface sensors over time;
converting the electrical signals from each of the plurality of surface sensors into contraction intensity information;
creating a movie comprising a plurality of uterine contractile maps based on the location of each of the plurality of surface sensors;
determining a center of uterine electrical activity based on the plurality of contractile maps;
tracking movement of the center of uterine electrical activity to establish a contraction pattern, wherein the contraction pattern is based at least in part on a percentage of time the contraction pattern occurs within a period of time; and
based on clinically relevant findings stemming from the contraction pattern, diagnosing normal or abnormal labor.

18. The computer program product of claim 17, wherein the computer software, when executed, further causes the processor of the uterine monitoring system to perform the step of: sequentially analyzing the plurality of uterine contractile maps to extract information about the contraction pattern.

19. The computer program product of claim 18, wherein the computer software, when executed, further causes the processor of the uterine monitoring system to perform the step of:
extracting the information about the contraction pattern including time and location a contraction starts, extent of the contraction, a direction of contractile propagation, and a spread and a speed of contractile propagation over the patient's abdomen from the plurality of uterine contractile maps.

20. The computer program product of claim 18, wherein the computer software, when executed, further causes the processor of the uterine monitoring system to perform the steps of:

analyzing the electrical signals to extract the following parameters from a grid of locations corresponding to the plurality of surface sensors: time of contraction, location of contraction, extent of contraction, direction of propagation, speed of propagation over the abdomen, average contraction amplitude of an electrohysterogram (EHG) envelope over time, spatial location of the peak of contraction and variance, spread of the contraction, abdominal intensity distribution, abdominal frequency distribution, patterns of contraction intensity over time, distance of peak power propagation, power changes over time, and frequency changes over time from the sequentially analyzed plurality of uterine contractile maps; and using the parameters to quantify the contraction pattern to predict labor outcome.

\* \* \* \* \*